United States Patent [19]

Teulon

[11] Patent Number: 4,755,509

[45] Date of Patent: Jul. 5, 1988

[54] HETEROCYCLIC ALDOSE REDUCTASE INHIBITORS AND METHODS OF USING THEM

[75] Inventor: Jean-Marie Teulon, Celle Saint Cloud, France

[73] Assignee: Carbipem, Rueil Malmaison, France

[21] Appl. No.: 733,685

[22] Filed: May 14, 1985

[30] Foreign Application Priority Data

May 18, 1984 [FR] France .................. 84 07791
Mar. 5, 1985 [FR] France .................. 85 03236

[51] Int. Cl.$^4$ .................. C07D 279/16; A61K 31/54
[52] U.S. Cl. .................. 514/224.2; 544/52
[58] Field of Search .................. 544/52; 514/225

[56] References Cited

U.S. PATENT DOCUMENTS 3,923,709 12/1975 Worley .................. 544/52
4,512,990 4/1985 Nelson et al. .................. 544/52
4,584,300 4/1986 Iwao et al. .................. 544/52

FOREIGN PATENT DOCUMENTS 116368 8/1984 European Pat. Off. .............. 544/52
1173942 12/1969 United Kingdom .

OTHER PUBLICATIONS

Shridhar et al., *Chemical Abstracts*, 101, 55016u (1984).
Lipinski and Hutson, "Aldose Reductase Inhibitors as a New Approach to the Treatment of Diabetic Complications", (Sep. 11, 1984), *Annual Reports in Medicinal Chemistry*, 19 196.
Kador, Kinoshita and Sharpless, "Aldose Reductase Inhibitors: A Potential New Class of Agents for the Pharmacological Control of Certain Diabetic Complications", (Jul. 1985), *Journal of Medicinal Chemistry*, 28 841.
Kador, Robison and Kinoshita, "The Pharmacology of Aldose Reductase Inhibitors", (1985), *Ann. Rev. Pharmacol. Toxicol.*, 25, 691.

*Primary Examiner*—John M. Ford
*Attorney, Agent, or Firm*—Wannell M. Crook

[57] ABSTRACT

The invention relates to new compounds of the formula:

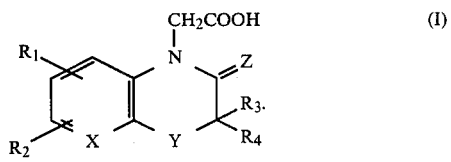

Aldose reductase inhibitors.

Treatment of certain complications of diabetes.

29 Claims, No Drawings

HETEROCYCLIC ALDOSE REDUCTASE INHIBITORS AND METHODS OF USING THEM

The present invention relates to heterocyclic derivatives of the formula (I). It also relates to the processes for the preparation of the said products and to their applications in therapy.

The new compounds according to the invention are chosen from the group consisting of the compounds of the general formula (I):

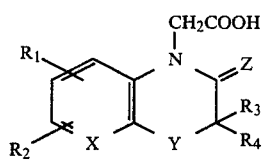

in which:
- Z represents the sulfur atom but can also represent oxygen when Y represents sulfur or when $X=Y=N$;
- Y represents the oxygen atom or the sulfur atom or a methylene; Y can also represent the nitrogen atom when X is nitrogen;
- X represents CH or the nitrogen atom;
- $R_1$ and $R_2$ can represent hydrogen, a halogen or a trifluoromethyl, methoxy, thiomethyl, thiotrifluoromethyl or trifluoromethoxy group; and
- $R_3$ and $R_4$ can represent hydrogen, a lower alkyl or an optionally substituted phenyl or pyridyl nucleus; "lower alkyl" is understood as meaning a branched or unbranched $C_1$-$C_5$ group.

The compounds of the formula (I) according to the invention can be synthesized by the hydrolysis, in a basic or acidic medium, of esters of the formula (II):

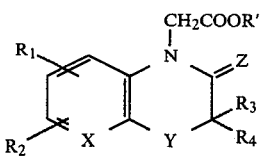

in which $R_1$, $R_2$, $R_3$, $R_4$, X, Y and Z are defined as above, R' being a lower alkyl group.

The basic agent can be sodium hydroxide, potassium hydroxide, sodium or potassium carbonate or sodium or potassium bicarbonate. The acidic agent can be a conventional acid such as hydrochloric acid. The saponification will be carried out in an aqueous-alcoholic medium, tetrahydrofuran/water, dioxane/water or a water-miscible solvent. The hydrolysis temperature will be between 25° and 100° C. For the derivatives in which $Z=S$, the optimum method will be to use sodium hydroxide or potassium hydroxide in an aqueous-alcoholic medium at 25° C. or potassium bicarbonate in an aqueous-alcoholic medium at the boil.

The compounds of the formula (II) in which $Z=S$ are synthesized from the derivatives in which $Z=O$ by reaction with $P_2S_5$ in a conventional organic solvent such as methylene chloride, chloroform, benzene, toluene, xylene, pyridine, tetrahydrofuran, dioxane, acetonitrile or HMPT, in the presence or absence of a base such as sodium or potassium bicarbonate or triethylamine, at a temperature of between 20° and 140° C., or by reaction with Lawesson's reagent or an analogous thiolation reagent in an organic solvent such as benzene, toluene, xylene or dimethoxyethane, at a temperature of between 20° and 140° C. The optimum method will be to use $P_2S_5$ in chloroform at a temperature of between 20° and 61° C.

The esters of the formula II in which $Z=O$ are obtained by reacting an alkyl halogenoacetate with the NH derivatives of the formula III which have been metallated beforehand with common metallating agents, in solvents conventional for this type of reaction, such as, for example, dimethylformamide:

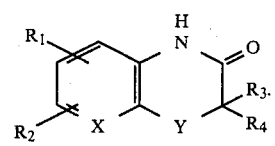

In the formula III, $R_1$, $R_2$, $R_3$, $R_4$, X and Y are defined as above.

The derivatives of the formula III are obtained by the cyclization of the amino esters or amino acids of the formula IV:

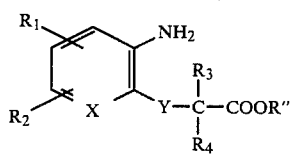

in which $R_1$, $R_2$, $R_3$, $R_4$, X and Y are defined as above, R" being hydrogen or a lower alkyl.

The derivatives of the formula III in which $Y=S$ can also be synthesized directly by reacting a derivative of the formula V with an alkyl halogenoacetate or the acid or its acid chloride of the formula VI:

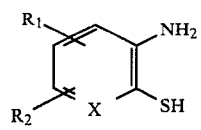

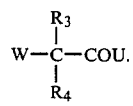

In the formula V, $R_1$, $R_2$ and X are defined as above; in the formula VI, $R_3$ and $R_4$ are defined as above, W represents a halogen and U represents OH, OR" or chlorine, R" being defined as above.

The derivatives of the formula III in which $Y=CH_2$ and $X=CH$ can also be synthesized by the acid cyclization, in a method known per se, for example the aluminum chloride method, of derivatives of the formula VII:

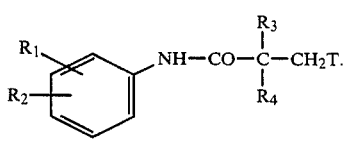

In the formula VII, $R_1$, $R_2$, $R_3$ and $R_4$ are defined as above and T represents the chlorine or bromine atom.

The compounds of the formula IV are synthesized by the hydrogenation of the nitro derivatives of the formula VIII:

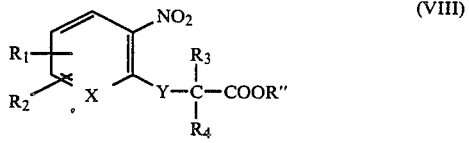

in which $R_1$, $R_2$, $R_3$, $R_4$, X, Y and R'' are defined as above.

The derivatives of the formula VIII are obtained, in the case where Y=N, by reacting a glycine ester, or, in the case where Y=S, by reacting a mercaptoacetic acid ester or the acid itself with the nitro derivatives of the formula IX:

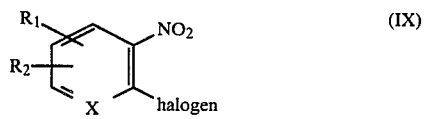

in which $R_1$, $R_2$ and X are defined as above, and, in the case where Y=O when X=CH, or Y=S, the said derivatives can also be obtained by reacting an appropriately substituted alkyl halogenoacetate with a derivative of the formula X, metallated beforehand if necessary:

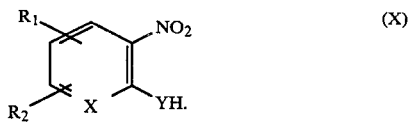

In the formula X, $R_1$, $R_2$, X and Y are defined as above.

According to the invention, therapeutic compositions are proposed which are useful especially for the treatment of peripheral disorders consequent upon diabetes (cataract, neuropathy), which compositions contain, in association with a physiologically acceptable excipient, at least one compound of the formula I or one of its non-toxic addition salts.

For all the derivatives of the invention, it will be possible to salify the acid group with an alkali metal or an alkaline earth metal, such as sodium or potassium, a base such as an amine like dicyclohexylamine, an amino alcohol such as aminoethanol, or an amino acid such as lysine.

If X=Y=N, the salification can be carried out for example with an acid such as HCl, HBr or an organic acid normally used for this purpose.

Further characteristics and advantages of the invention will be understood more clearly from the following description of some preparation examples which in no way imply a limitation but are given by way of illustration.

Table II below shows the structural formulas of some of the products.

EXAMPLE 1

Ethyl 3-nitropyridine-2-mercaptoacetate

Formula VIII: $R_1=R_2=R_3=R_4=H$; X=N; Y=S; R''=$C_2H_5$

A solution of 50 g of 3-nitro-2-chloropyridine and 38 g of ethyl mercaptoacetate in 400 ml of ethanol containing 30 g of sodium bicarbonate is heated under reflux for 7 hours. The solution is subsequently concentrated in vacuo and then, after cooling, the residue is treated with water and ice and extracted with ether. The ether phase is washed with water and dried, the solvent is evaporated off and a residue is recovered which crystallizes from isopropyl ether. The crystals are filtered off and dried to give 49 g of ethyl 3-nitropyridine-2-mercaptoacetate in the form of crystals of melting point 58° C.

EXAMPLE 2

Ethyl 6-chloro-3-nitropyridine-2-mercaptoacetate

Formula VIII: $R_1$=6-chloro; $R_2=R_3=R_4=H$; X=N; Y=S; R''=$C_2H_5$

Following the procedure of Example 1, but using 25 g of 90% pure 2,6-dichloro-3-nitropyridine and 14 g of ethyl mercaptoacetate, 32.5 g of ethyl 6-chloro-3-nitropyridine-2-mercaptoacetate are obtained in the form of an oil which is used in the crude state for the next step.

EXAMPLE 3

3-Nitropyridine-2-mercapto-α-methylacetic acid

Formula VIII: $R_1=R_2=R_3=H$; $R_4=CH_3$; X=N; Y=S; R''=H

Following the procedure of Example 1, but using 46 g of 3-nitro-2-chloropyridine and 32 g of 2-mercaptopropionic acid, 50 g of 3-nitropyridine-2-mercapto-α-methylacetic acid are obtained, after acidification with acetic acid, in the form of crystals of melting point 135° C.

EXAMPLE 4

Ethyl 3-nitropyridine-2-aminoacetate

Formula VIII: $R_1=R_2=R_3=R_4=H$; X=Y=N; R''=$C_2H_5$

A solution of 20 g of 3-nitro-2-chloropyridine and 32 g of ethyl glycinate in 100 ml of ethanol is heated under reflux for 3 hours. The solution is then concentrated in vacuo and, after cooling followed by the addition of water and ice, the residue is extracted with ether. The ether phase is washed with water and then dried and the ether is evaporated off in vacuo. 28 g of ethyl 3-nitropyridine-2-aminoacetate are recovered in the form of an oil which is used in the crude state for the next step.

EXAMPLE 5

Ethyl 4-trifluoromethyl-2-nitrophenylthioacetate

Formula VIII: $R_1$=4-$CF_3$; $R_2=R_3=R_4=H$; X=CH; Y=S; R''=$C_2H_5$

Following the procedure of Example 1, but using 38 g of 4-trifluoromethyl-2-nitrochlorobenzene and 21.5 g of ethyl mercaptoacetate, 29 g of ethyl 4-trifluoromethyl-2-nitrophenylthioacetate are obtained, after distillation of the residue [boiling point (2 mm Hg)=155°-160° C.], in the form of crystals of melting point 42°-45° C.

EXAMPLE 6

Ethyl 5-fluoro-2-nitrophenylthioacetate

Formula VIII: $R_1=5\text{-F}$; $R_2=R_3=R_4=\text{H}$; $X=\text{CH}$; $Y=\text{S}$; $R'=C_2H_5$ Following the procedure of Example 1, but using 83 g of 2,4-difluoronitrobenzene and 63 g of ethyl mercaptoacetate, 85 g of ethyl 5-fluoro-2-nitrophenylthioacetate are obtained, after distillation of the residue [boiling point (1 mm Hg)=155°-160° C.], in the form of crystals of melting point 58° C.

EXAMPLE 7

Ethyl 4-fluoro-2-nitrophenylthioacetate

Formula VIII: $R_1=4\text{-F}$; $R_2=R_3=R_4=\text{H}$; $X=\text{CH}$; $Y=\text{S}$; $R''=C_2H_5$ Following the procedure of Example 1, but starting from 73 g of 2,5-difluoronitrobenzene and 56 g of ethyl mercaptoacetate, 75 g of ethyl 4-fluoro-2-nitrophenylthioacetate are obtained, after crystallization of the residue from pentane, in the form of crystals of melting point <50° C.

EXAMPLE 8

Ethyl 6-chloro-2-nitrophenylthioacetate

Formula VIII: $R_1=6\text{-Cl}$; $R_2=R_3=R_4=\text{H}$; $X=\text{CH}$; $Y=\text{S}$; $R''=C_2H_5$ Following the procedure of Example 1, but using 100 g of 2,3-dichloronitrobenzene and 63 g of ethyl mercaptoacetate, 22.5 g of ethyl 6-chloro-2-nitrophenylthioacetate are obtained, after filtration on silica gel, in the form of an oil which is used in the crude state for the next step.

EXAMPLE 9

Ethyl 4-methoxy-2-nitrophenylthioacetate

Formula VIII: $R_1=4\text{-OCH}_3$; $R_2=R_3=R_4=\text{H}$; $X=\text{CH}$; $Y=\text{S}$; $R''=C_2H_5$ Following the procedure of Example 1, but starting from 100 g of 2-chloro-5-methoxynitrobenzene and 68 g of ethyl mercaptoacetate, 55 g of ethyl 4-methoxy-2-nitrophenylthioacetate are obtained, after crystallization of the residue from isopropyl ether, in the form of crystals of melting point 75° C.

EXAMPLE 10

Ethyl 4-trifluoromethyl-5-chloro-2-nitrophenylthioacetate

Formula VIII: $R_1=4\text{-CF}_3$; $R_2=5\text{-Cl}$; $R_3=R_4=\text{H}$; $X=\text{CH}$; $Y=\text{S}$; $R''=C_2H_5$ Following the procedure of Example 1, but starting from 50 g of 2,4-dichloro-5-trifluoromethylnitrobenzene and 23 g of ethyl mercaptoacetate, 56 g of ethyl 4-trifluoromethyl-5-chloro-2-nitrophenylthioacetate are obtained in the form of crystals of melting point 85° C.

EXAMPLE 11

Ethyl 5-chloro-2-nitrophenylthioacetate

Formula VIII: $R_1=5\text{-Cl}$; $R_2=R_3=R_4=\text{H}$; $X=\text{CH}$; $Y=\text{S}$; $R''=C_2H_5$ Following the procedure of Example 1, but using 68.8 g of 2,4-dichloronitrobenzene and 43 g of ethyl mercaptoacetate, 45 g of ethyl 5-chloro-2-nitrophenylthioacetate are obtained, after filtration on silica gel, in the form of crystals of melting point 48°-50° C.

EXAMPLE 12

Ethyl 4-chloro-2-nitrophenylthioacetate

Formula VIII: $R_1=4\text{-Cl}$; $R_2=R_3=R_4=\text{H}$; $X=\text{CH}$; $Y=\text{S}$; $R''=C_2H_5$ Following the procedure of Example 1, but using 100 g of 2,5-dichloronitrobenzene and 63 g of ethyl mercaptoacetate, 52 g of ethyl 4-chloro-2-nitrophenylthioacetate are obtained, after crystallization of the residue from a pentane/isopropyl ether mixture, in the form of crystals of melting point 52° C.

EXAMPLE 13

4-Fluoro-2-nitrophenylthio-α-methylacetic acid

Formula VII: $R_1=4\text{-F}$; $R_3=\text{CH}_3$; $R_2=R_4=\text{H}$; $X=\text{CH}$; $Y=\text{S}$; $R''=\text{H}$ Following the procedure of Example 1, but using 15.9 g of 2,5-difluoronitrobenzene and 11 g of 2-mercaptopropionic acid, 21 g of 4-fluoro-2-nitrophenylthio-α-methylacetic acid are obtained, after acidification with acetic acid, in the form of crystals of melting point 116° C.

EXAMPLE 14

4-Chloro-2-nitrophenylthio-α-methylacetic acid

Formula VIII: $R_1=4\text{-Cl}$; $R_3=\text{CH}_3$; $R_2=R_4=\text{H}$; $X=\text{CH}$; $Y=\text{S}$; $R''=\text{H}$ Following the procedure of Example 1, but using 38.4 g of 2,5-dichloronitrobenzene and 22 g of 2-mercaptopropionic acid, 32 g of 4-chloro-2-nitrophenylthio-α-methylacetic acid are obtained, after acidification with acetic acid, in the form of crystals of melting point 114° C.

EXAMPLE 15

Ethyl 4-chloro-2-nitrophenylthio-α-phenylacetate

Formula VIII: $R_1=4\text{-Cl}$; $R_3=\text{phenyl}$; $R_2=R_4=\text{H}$; $X=\text{CH}$; $Y=\text{S}$; $R''=C_2H_5$ A solution of 14 g of ethyl α-bromophenylacetate in 10 ml of ethanol is added dropwise, with stirring, to a solution of 10.5 g of 2-nitro-4-chlorothiophenol in 100 ml of ethanol containing 2.2 g of sodium hydroxide dissolved in 10 ml of water. After the addition has ended, stirring is continued for 3 hours at ambient temperature and the precipitate formed is then filtered off, washed with a small quantity of ethanol, with a 5% aqueous solution of sodium hydroxide and then with water and dried. 11.5 g of ethyl 4-chloro-2-nitrophenylthio-α-phenylacetate are thus recovered in the form of crystals of melting point 112° C.

EXAMPLE 16

5-Chloro-2-nitrophenylthio-α-methylacetic acid

Formula VIII: $R_1=5$-Cl; $R_3=CH_3$; $R_2=R_4=H$; $X=CH$; $Y=S$; $R''=H$

Following the procedure of Example 1, but using 100 g of 2,4-dichloronitrobenzene and 55 g of 2-mercaptopropionic acid, 76 g of 5-chloro-2-nitrophenylthio-α-methylacetic acid are obtained, after acidification with acetic acid and crystallization of the residue from an isopropyl ether/pentane mixture, in the form of crystals of melting point 125° C.

EXAMPLE 17

Ethyl 4,5-dichloro-2-nitrophenylthioacetate

Formula VIII: $R_1=4$-Cl; $R_2=5$-Cl; $R_3=R_4=H$; $X=CH$; $Y=S$; $R''=C_2H_5$

Following the procedure of Example 1, but using 93.2 g of 2,4,5-trichloronitrobenzene and 42 g of ethyl mercaptoacetate, 68 g of a mixture of ethyl 4,5-dichloro-2-nitrophenylthioacetate and ethyl 2,5-dichloro-4-nitrophenylthioacetate are obtained after filtration on silica gel and are used in the crude state for the next step.

EXAMPLE 18

Ethyl 4-fluoro-2-nitrophenoxyacetate

Formula VIII: $R_1=4$-F; $R_2=R_3=R_4=H$; $X=CH$; $Y=O$; $R''=CH_2H_5$

A solution of 14 g of sodium hydroxide in 30 ml of water is added dropwise to a solution of 54.7 g of 4-fluoro-2-nitrophenol in 400 ml of ethanol. The reaction mixture is then cooled with an ice bath and 40 ml of ethyl chloroacetate are added dropwise, with stirring. The mixture is subsequently left to return to ambient temperature, after which it is stirred for 4 hours and then heated under reflux for a further four hours, still with stirring.

The reaction mixture is then concentrated in vacuo, the residue is taken up with water and ice and extracted with ether, and the ether extract is washed with water, with dilute sodium hydroxide solution and then again with water and dried. The ether is evaporated off and 46 g of ethyl 4-fluoro-2-nitrophenoxyacetate are recovered in the form of an oil which is used in the crude state for the next step.

EXAMPLE 19

Ethyl 4-fluoro-2-nitrophenylthio-α-methylacetate

Formula VIII: $R_1=4$-F; $R_3=CH_3$; $R_2=R_4=H$; $X=CH$; $Y=S$; $R''=C_2H_5$

A solution of 44.3 g of 4-fluoro-2-nitrophenylthio-α-methylacetic acid, prepared in Example 13, in 300 ml of ethanol containing 10 ml of concentrated sulfuric acid is heated under reflux for 5 hours. The reaction mixture is then concentrated in vacuo, the residue is taken up with water and extracted with ether, and the ether extract is washed with a 5% aqueous solution of ammonia and then again with water and dried. After evaporation of the ether, 46.5 g of ethyl 4-fluoro-2-nitrophenylthio-α-methylacetate are recovered in the form of an oil which is used in the crude state for the next step.

EXAMPLE 20

Ethyl 4-chloro-2-nitrophenylthio-α-methylacetate

Formula VIII: $R_1=4$-Cl; $R_3=CH_3$; $R_2=R_4=H$; $X=CH$; $Y=S$; $R''=C_2H_5$

Following the procedure of Example 19, but starting from 32 g of 4-chloro-2-nitrophenylthio-α-methylacetic acid prepared in Example 14, 34 g of ethyl 4-chloro-2-nitrophenylthio-α-methylacetate are obtained in the form of an oil which is used in the crude state for the next step.

EXAMPLE 21

Ethyl 5-chloro-2-nitrophenylthio-α-methylacetate

Formula VIII: $R_1=5$-Cl; $R_3=CH_3$; $R_2=R_4=H$; $X=CH$; $Y=S$; $R''=C_2H_5$

Following the procedure of Example 19, but starting from 76 g of 5-chloro-2-nitrophenylthio-α-methylacetic acid prepared in Example 16, 72 g of ethyl 5-chloro-2-nitrophenylthio-α-methylacetate are obtained in the form of an oil which is used in the crude state for the next step.

EXAMPLE 22

1H-Pyrido[2,3-b][1,4]thiazin-2(3H)-one

Formula III: $R_1=R_2=R_3=R_4H$; $X=N$; $Y=S$

A solution of 49 g of ethyl 3-nitropyridine-2-mercaptoacetate, prepared in Example 1, in 500 ml of methanol is hydrogenated under atmospheric pressure in the presence of Raney nickel. After absorption of the theoretical quantity of hydrogen, the catalyst is filtered off and the solution is concentrated in vacuo, after which the residue is taken up with xylene and heated under reflux for 16 hours. After cooling following by the addition of hexane, the crystals formed are filtered off and then dried. 24 g of 1H-pyrido[2,3-b][1,4]thiazin-2(3H)-one are recovered in the form of crystals of melting point 207° C.

EXAMPLE 23

6-Chloro-1H-pyrido[2,3-b][1,4]thiazin-2(3H)-one

Formula III: $R_1=6$-chloro; $R_2=R_3=R_4=H$; $X=N$; $Y=S$

Following the procedure of Example 22, but starting from 14 g of ethyl 6-chloro-3-nitropyridine-2-mercaptoacetate prepared in Example 2, 4.1 g of 6-chloro-1H-pyrido[2,3-b][1,4]thiazin-2(3H)-one are recovered in the form of crystals of melting point 240°–245° C.

EXAMPLE 24

3-Methyl-1H-pyrido[2,3-b][1,4]thiazin-2(3H)-one

Formula III: $R_1=R_2=R_3=H$; $R_4=CH_3$; $X=N$; $Y=S$

Following the procedure of Example 22, but starting from 30 g of 3-nitropyridine-2-mercapto-α-methylacetic acid prepared in Example 3, 16 g of 3-methyl-1H-pyrido[2,3-b][1,4]thiazin-2(3H)-one are recovered in the form of crystals of melting point 178° C.

EXAMPLE 25

1H-Pyrido[2,3-b][1,4]pyrazin-2(3H)-one

Formula III: $R_1=R_2=R_3=R_4=H$; $X=Y=N$

Following the procedure of Example 22, but starting from 33 g of ethyl 3-nitropyridine-2-aminoacetate prepared in Example 4, 19 g of 1H-pyrido[2,3-b][1,4]pyrazin-2(3H)-one are obtained in the form of crystals of melting point 278°–282° C.

EXAMPLE 26

6-Trifluoromethyl-2H-1,4-benzothiazin-3(4H)-one

Formula III: $R_1=6\text{-}CF_3$; $R_2=R_3=R_4=H$; $X=CH$; $Y=S$

Following the procedure of Example 22, but starting from 29 g of ethyl 4-trifluoromethyl-2-nitrophenylacetate prepared in Example 5, 15 g of 6-trifluoromethyl-2H-1,4-benzothiazin-3(4H)-one are recovered in the form of crystals of melting point 190° C.

EXAMPLE 27

7-Fluoro-2H-1,4-benzothiazin-3(4H)-one

Formula III: $R_1=7\text{-}F$; $R_2=R_3=R_4=H$; $X=CH$; $Y=S$

Following the procedure of Example 22, but starting from 90 g of ethyl 5-fluoro-2-nitrophenylthioacetate prepared in Example 6, 45 g of 7-fluoro-2H-1,4-benzothiazin-3(4H)-one are obtained in the form of crystals of melting point 215° C.

EXAMPLE 28

6-Fluoro-2H-1,4-benzothiazin-3(4H)-one

Formula III: $R_1=6\text{-}F$; $R_2=R_3=R_4=H$; $X=CH$; $Y=S$

A solution of 75 g of ethyl 4-fluoro-2-nitrophenylthioacetate, prepared in Example 7, in 1 liter of methanol is hydrogenated under atmospheric pressure in the presence of Raney nickel. After absorption of the theoretical quantity of hydrogen, the catalyst is filtered off and the solution is concentrated in vacuo, after which the residue is taken up with 250 ml of water at 50° C. and 60 ml of concentrated hydrochloric acid and stirred for 30 minutes. The crystals formed are filtered off, washed with water and then with pentane and dried. 46 g of 6-fluoro-2H-1,4-benzothiazin-3(4H)-one are thus recovered in the form of crystals of melting point 189° C.

EXAMPLE 29

8-Chloro-2H-1,4-benzothiazin-3(4H)-one

Formula III: $R_1=8\text{-}Cl$; $R_2=R_3=R_4=H$; $X=CH$; $Y=S$

Following the procedure of Example 28, but using 22.5 g of ethyl 6-chloro-2-nitrophenylthioacetate prepared in Example 8, 12 g of 8-chloro-2H-1,4-benzothiazin-3(4H)-one are obtained in the form of crystals of melting point 222° C.

EXAMPLE 30

7-Chloro-2H-1,4-benzothiazin-3(4H)-one

Formula III: $R_1=7\text{-}Cl$; $R_2=R_3=R_4=H$; $X=CH$; $Y=S$

Following the procedure of Example 28, but using 42 g of ethyl 5-chloro-2-nitrophenylthioacetate prepared in Example 11, 23 g of 7-chloro-2H-1,4-benzothiazin-3(4H)-one are obtained in the form of crystals of melting point 210° C.

EXAMPLE 31

6-Methoxy-2H-1,4-benzothiazin-3(4H)-one

Formula III: $R_1=6\text{-}OCH_3$; $R_2=R_3=R_4=H$; $H=CH$; $Y=S$

Following the procedure of Example 28, but using 45 g of ethyl 4-methoxy-2-nitrophenylthioacetate prepared in Example 9, 27 g of 6-methoxy-2H-1,4-benzothiazin-3(4H)-one are obtained in the form of crystals of melting point 180°–182° C.

EXAMPLE 32

6-Trifluoromethyl-7-chloro-2H-1,4-benzothiazin-3(4H)-one

Formula III: $R_1=6\text{-}CF_3$; $R_2=7\text{-}Cl$; $R_3=R_4=H$; $X=CH$; $Y=S$

Following the procedure of Example 28, but using 56 g of ethyl 4-trifluoromethyl-5-chloro-2-nitrophenylthioacetate prepared in Example 10, 30 g of 6-trifluoromethyl-7-chloro-2H-1,4-benzothiazin-3(4H)-one are obtained, after recrystallization from methanol, in the form of crystals of melting point 234°–235° C.

EXAMPLE 33

2H-1,4-Benzothiazin-3(4H)-one

Formula III: $R_1=R_2=R_3=R_4=H$; $X=CH$; $Y=S$

A solution of sodium ethylate is prepared by dissolving 4.6 g of sodium in 200 ml of absolute ethanol. 25 g of orthoaminothiophenol are added dropwise to this solution, then, after the addition has ended, the mixture is stirred for 10 minutes and cooled with an ice bath and 24 ml of ethyl bromoacetate are then added dropwise. After the addition has ended, the mixture is stirred for 3 hours at ambient temperature, the sodium bromide formed is then filtered off and the filtrate is concentrated in vacuo. The residue obtained crystallizes from ether. The crystals are filtered off and dried to give 23 g of 2H-1,4-benzothiazin-3(4H)-one in the form of crystals of melting point 177° C.

EXAMPLE 34

2-Methyl-2H-1,4-benzothiazin-3(4H)-one

Formula III: $R_1=R_2=R_3=H$; $R_4=CH_3$; $X=CH$; $Y=S$

A solution of 24 g of sodium hydroxide dissolved in the minimum quantity of water is added to a solution of 37.5 g of orthoaminothiophenol in 100 ml of ethanol, the mixture is stirred for 10 minutes and cooled with an ice bath and a solution of 45.9 g of α-bromopropionic acid in 50 ml of ethanol is then added dropwise. The reaction mixture is left to return to ambient temperature and then heated under reflux for 4 hours. After concentration in vacuo, water is added followed by hydrochloric acid until the pH is acid, and the crystals formed are filtered off, washed with water and then dried. 41.7 g of 2-methyl-2H-1,4-benzothiazin-3(4H)-one are thus recovered in the form of crystals of melting point 126°–127° C.

EXAMPLE 35

2-Phenyl-2H-1,4-benzothiazin-3(4H)-one

Formula III: $R_1=R_2=R_3=H$; $R_4=$phenyl; $X=CH$; $Y=S$

Following the procedure of Example 34, but using 12.5 g of orthoaminothiophenol and 17 g of α-chlorophenylacetic acid, 9.7 g of 2-phenyl-2H-1,4-benzothiazin-3(4H)-one are obtained in the form of crystals of melting point 194° C.

EXAMPLE 36

6-Chloro-2H-1,4-benzothiazin-3(4H)-one

Formula III: $R_1=6$-Cl; $R_2=R_3=R_4=H$; $X=CH$; $Y=S$

Following the procedure of Example 28, but using 52 g of ethyl 4-chloro-2-nitrophenylthioacetate prepared in Example 12, 27.3 g of 6-chloro-2H-1,4-benzothiazin-3(4H)-one are obtained in the form of crystals of melting point 208° C.

EXAMPLE 37

6-Fluoro-2-methyl-2H-1,4-benzothiazin-3(4H)-one

Formula III: $R_1=6$-F; $R_3=CH_3$; $R_2=R_4=H$; $X=CH$; $Y=S$

Following the procedure of Example 28, but using 55 g of ethyl 4-fluoro-2-nitrophenylthio-α-methylacetate prepared in Example 19, 31 g of 6-fluoro-2-methyl-2H-1,4-benzothiazin-3(4H)-one are obtained, after recrystallization from isopropanol, in the form of crystals of melting point 164° C.

EXAMPLE 38

6-Chloro-2-methyl-2H-1,4-benzothiazin-3(4)-one

Formula III: $R_1=6$-Cl; $R_3=CH_3$; $R_2=R_4=H$; $X=CH$; $Y=S$

Following the procedure of Example 28, but using 34 g of ethyl 4-chloro-2-nitrophenylthio-α-methylacetate prepared in Example 20, 19 g of 6-chloro-2-methyl-2H-1,4-benzothiazin-3(4H)-one are obtained in the form of crystals of melting point 188° C.

EXAMPLE 39

6-Chloro-2-phenyl-2H-1,4-benzothiazin-3(4H)-one

Formula III: $R_1=6$-Cl; $R_3=$phenyl; $R_2=R_4=H$; $X=CH$; $Y=S$

Following the procedure of Example 28, but using 11.5 g of ethyl 4-chloro-2-nitrophenylthio-α-phenylacetate prepared in Example 15, 4 g of 6-chloro-2-phenyl-2H-1,4-benzothiazin-3(4H)-one are obtained in the form of crystals of melting point 216° C.

EXAMPLE 40

2,2-Dimethyl-2H-1,4-benzothiazin-3(4H)-one

Formula III: $R_1=R_2=H$; $R_3=R_4=CH_3$; $X=CH$; $Y=S$

Following the procedure of Example 34, but starting from 90 g of orthoaminothiophenol, 28.8 g of sodium hydroxide and 140.4 g of ethyl α-bromoisobutyrate, 112 g of 2,2-dimethyl-2H-1,4-benzothiazin-3(4H)-one are obtained in the form of crystals of melting point 155° C.

EXAMPLE 41

2-Parachlorophenyl-2H-1,4-benzothiazin-3(4H)-one

Formula III: $R_1=R_2=R_3=H$; $R_4=$parachlorophenyl; $X=CH$; $Y=S$

Following the procedure of Example 34, but starting from 25 g of orthoaminothiophenol, 8 g of sodium hydroxide and 55 g of ethyl α-bromoparachlorophenylacetate, 37.8 g of 2-parachlorophenyl-2H-1,4-benzothiazin-3(4H)-one are obtained in the form of crystals of melting point 198° C.

EXAMPLE 42

2-Orthochlorophenyl-2H-1,4-benzothiazin-3(4H)-one

Formula III: $R_1=R_2=R_3=H$; $R_4=$orthochlorophenyl; $X=CH$; $Y=S$

Following the procedure of Example 34, but starting from 25 g of orthoaminothiophenol, 8 g of sodium hydroxide and 55 g of ethyl α-bromoorthochlorophenylacetate; 37 g of 2-orthochlorophenyl-2H-1,4-benzothiazin-3(4H)-one are obtained in the form of crystals of melting point 200° C.

EXAMPLE 43

6,7-Dichloro-2H-1,4-benzothiazin-3(4H)-one

Formula III: $R_1=6$-Cl; $R_2=7$-Cl; $R_3=R_4=H$; $X=CH$; $Y=S$

Following the procedure of Example 28, but starting from a mixture of 68 g of ethyl 4,5-dichloro-2-nitrophenylthioacetate and ethyl 2,5-dichloro-4-nitrophenylthioacetate prepared in Example 17, 4.5 g of 6,7-dichloro-2H-1,4-benzothiazin-3(4H)-one are obtained in the form of crystals of melting point 251°-253° C.

EXAMPLE 44

2-Methyl-2-(pyridin-2'-yl)-2H-1,4-benzothiazin-3(4H)-one

Formula III: $R_1=R_2=H$; $R_3=CH_3$; $R_4=$pyridin-2'-yl; $X=CH$; $Y=S$

A solution of sodium ethylate is prepared by dissolving 4 g of sodium in 300 ml of absolute ethanol. 21.5 g of orthoaminothiophenol are added dropwise to this solution and then, after the addition has ended, the mixture is stirred for 10 minutes. It is cooled with an ice bath and 40 g of ethyl α-bromo-α-methylpyridin-2-ylacetate are then added dropwise; after the addition has ended, the mixture is left to return to ambient temperature, stirring is then continued for 4 hours and the mixture is left to stand overnight. The precipitate formed is filtered off, washed with water and then with ethanol and dried. 25.3 g of 2-methyl-2-(pyridin-2'-yl)-2H-1,4-benzothiazin-3(4H)-one are thus recovered in the form of crystals of melting point 217°-219° C.

EXAMPLE 45

6-Fluoro-2H-1,4-benzoxazin-3(4H)-one

Formula III: $R_1=6$-F; $R_2=R_3=R_4=H$; $X=CH$; $Y=O$

A solution of 46 g of ethyl 4-fluoro-2-nitrophenoxyacetate, prepared in Example 18, in 500 ml of methanol is hydrogenated under atmospheric pressure in the presence of Raney nickel. After absorption of the theoretical quantity of hydrogen, the catalyst is filtered off, the solution is concentrated in vacuo and the residue is taken up in either, from which it crystallizes. The crystals formed are filtered off, washed with ether and dried. 28 g of 6-fluoro-2H-1,4-benzoxazin-3(4H)-one are thus obtained in the form of crystals of melting point 206°–207° C.

EXAMPLE 46

6-Fluoro-3,4-dihydrocarbostyril

Formula III: $R_1=6\text{-F}$; $R_2=R_3=R_4=H$; $X=CH$; $Y=CH_2$ 31 g of N-(parafluorophenyl)-β-chloropropionamide are added, at between 180° and 220° C., to a mixture of 158 g of aluminum chloride and 40 g of sodium chloride and the reaction mixture is then stirred at this temperature for 30 minutes. The reaction mixture is then cooled on ice and the crystals formed are filtered off, washed with water and dried. After recrystallization from isopropanol, 14 g of 6-fluoro-3,4-dihydrocarbostyril are thus recovered in the form of crystals of melting point 180°–181° C.

EXAMPLE 47

6-Chloro-3,4-dihydrocarbostyril

Formula III: $R_1=6\text{-Cl}$; $R_2=R_3=R_4=H$; $X=CH$; $Y=CH_2$

Following the procedure of Example 46, but starting from 142.7 g of N-(parachlorophenyl)-β-chloropropionamide, 66.4 g of 6-chloro-3,4-dihydrocarbostyril are recovered, after recrystallization from acetonitrile, in the form of crystals of melting pont 163°–165° C.

EXAMPLE 48

7-Fluoro-3,4-dihydrocarbostyril

Formula III: $R_1=7\text{-F}$; $R_2=R_3=R_4=H$; $X=CH$; $Y=CH_2$

Following the procedure of Example 46, but starting from 90.4 g of N-(metafluorophenyl)-β-chloropropionamide, 35.8 g of 7-fluoro-3,4-dihydrocarbostyril are obtained, after recrystallization from isopropanol, in the form of crystals of melting point 187°–188° C.

EXAMPLE 49

7-Chloro-3,4-dihydrocarbostyril

Formula III: $R_1=7\text{-Cl}$; $R_2=R_3=R_4=H$; $X=CH$; $Y=CH_2$

Following the procedure of Example 46, but starting from 133.9 g of N-(metachlorophenyl)-β-chloropropionamide, 56 g of 7-chloro-3,4-dihydrocarbostyril are obtained, after recrystallization from acetonitrile, in the form of crystals of melting point 160°–165° C.

EXAMPLE 50

2-Parafluorophenyl-2H-1,4-benzothiazin-3(4H)-one

Formula III: $R_1=R_2=R_3=H$; $R_4=$parafluorophenyl; $X=CH$; $Y=S$

Following the procedure of Example 34, but starting from 20.7 g of orthoaminothiophenol, 6.7 g of sodium hydroxide and 43 g of ethyl α-bromoparafluorophenylacetate, 34.7 g of 2-parafluorophenyl-2H-1,4-benzothiazin-3(4H)-one are obtained in the form of crystals of melting point 215° C.

EXAMPLE 51

2-Orthofluorophenyl-2H-1,4-benzothiazin-3(4H)-one

Formula III: $R_1=R_2=R_3=H$; $R_4=$orthofluorophenyl; $X=CH$; $Y=S$

Following the procedure of Example 34, but starting from 20.7 g of orthoaminothiophenol, 6.7 g of sodium hydroxide and 43 g of ethyl α-bromoorthofluorophenylacetate, 33.5 g of 2-orthofluorophenyl-2H-1,4-benzothiazin-3(4H)-one are obtained in the form of crystals of melting point 177° C.

EXAMPLE 52

Ethyl pyrido[2,3-b][1,4]thiazin-2(3H)-one-1-acetate

Formula II: $R_1=R_2=R_3=R_4=H$; $X=N$; $Y=S$; $Z=O$; $R'=C_2H_5$

A solution of 12 g of 1H-pyrido[2,3-b][1,4]thiazin-2(3H)-one, prepared in Example 22, in 75 ml of dimethylformamide is added dropwise to a suspension of 3.5 g of sodium hydride in 30 ml of dimethylformamide. After the addition has ended, the mixture is stirred for 30 minutes and 9 ml of ethyl bromoacetate are then added dropwise; when the addition is complete, the mixture is stirred for a further 6 hours at ambient temperature and then, after the addition of water and ice, it is extracted with ether and the ether extract is washed carefully with water, dried and evaporated. The residue obtained crystallizes from an isopropyl ether/hexane mixture. The crystals are filtered off and dried. 9 g of ethyl pyrido[2,3-b][1,4]thiazin-2(3H)-one-1-acetate are obtained in the form of crystals of melting point 83° C.

EXAMPLE 53

Ethyl 6-chloropyrido[2,3-b][1,4]thiazin-2(3H)-one-1-acetate

Formula II: $R_1=6\text{-Cl}$; $R_2=R_3=H$; $X=N$; $Y=S$; $Z=O$; $R'=C_2H_5$

Following the procedure of Example 52, but starting from 4.1 g of 6-chloro-1H-pyrido[2,3-b][1,4]thiazin-2(3H)-one prepared in Example 23, 3.5 g of ethyl 6-chloropyrido[2,3-b][1,4]thiazin-2(3H)-one-1-acetate are obtained, after crystallization from isopropyl ether, in the form of crystals of melting point 105° C.

EXAMPLE 54

Ethyl 3-methylpyrido[2,3-b][1,4]thiazin-2(3H)-one-1-acetate

Formula II: $R_1=R_2=R_3=H$; $R_4=CH_3$; $X=N$; $Y=S$; $Z=0$; $R'=C_2H_5$

Following the procedure of Example 52, but starting from 15.7 g of 3-methyl-1H-pyrido[2,3-b][1,4]thiazin-2(3H)-one prepared in Example 24, 10 g of ethyl 3-methylpyrido[2,3-b][1,4]thiazin-2(3H)-one-1-acetate are obtained, after recrystallization from an isopropyl ether/acetone mixture, in the form of crystals of melting point 89° C.

EXAMPLE 55

Ethyl pyrido[2,3-b][1,4]pyrazin-2(3H)-one-1-acetate hydrochloride

Formula II: $R_1=R_2=R_3=R_4=H$; $X=Y=N$; $Z=O$; $R'=C_2H_5$

Following the procedure of Example 52, but starting from 12 g of 1H-pyrido[2,3-b][1,4]pyrazin-2-(3H)-one prepared in Example 25, the base, which has a melting point of 142° C., is obtained by extraction with chloroform and crystallization from an ether/petroleum ether mixture. This base is dissolved in an acetone/methanol mixture and treated with a solution of hydrogen chloride in ether until the pH is acid. The crystals formed are filtered off, washed with ether and dried. 7.8 g of ethyl pyrido[2,3-b][1,4]pyrazin-2(3H)-one-1-acetate hydrochloride are thus recovered in the form of crystals of melting point 207°–210° C.

EXAMPLE 56

Ethyl 6-trifluoromethyl-2H-1,4-benzothiazin-3-one-4-acetate

Formula II: $R_1=6\text{-}CF_3$; $R_2=R_3=R_4=H$; $X=CH$; $Y=S$; $Z=O$; $R'=C_2H_5$ Following the procedure of Example 52, but starting from 12 g of 6-trifluoromethyl-2H-benzothiazin-3(4H)-one prepared in Example 26, 8 g of ethyl 6-trifluoromethyl-2H-1,4-benzothiazin-3-one-4-acetate are obtained, after crystallization from pentane, in the form of crystals of melting point 60° C.

EXAMPLE 57

Ethyl 7-fluoro-2H-1,4-benzothiazin-3-one-4-acetate

Formula II: $R_1=7\text{-}F$; $R_2=R_3=R_4=H$; $X=CH$; $Y=S$; $Z=O$; $R'=C_2H_5$ Following the procedure of Example 52, but starting from 20 g of 7-fluoro-2H-1,4-benzothiazin-3-(4H)-one prepared in Example 27, 19 g of ethyl 7-fluoro-2H-1,4-benzothiazin-3-one-4-acetate are obtained, after crystallization from an ether/pentane mixture, in the form of crystals of melting point 85° C.

EXAMPLE 58

Ethyl 6-fluoro-2H-1,4-benzothiazin-3-one-4-acetate

Formula II: $R_1=6\text{-}F$; $R_2=R_3=R_4=H$; $X=CH$; $Y=S$; $Z=O$; $R'=C_2H_5$ Following the procedure of Example 52, but starting from 43 g of 6-fluoro-2H-1,4-benzothiazin-3(4H)-one prepared in Example 28, 36 g of ethyl 6-fluoro-2H-1,4-benzothiazin-3-one-4-acetate are obtained, after crystallization from an acetone/pentane mixture, in the form of crystals of melting point 80° C.

EXAMPLE 59

Ethyl 8-chloro-2H-1,4-benzothiazin-3-one-4-acetate

Formula II: $R_1=8\text{-}Cl$; $R_2=R_3=R_4=H$; $X=CH$; $Y=S$; $Z=O$; $R'=C_2H_5$ Following the procedure of Example 52, but starting from 12 g of 8-chloro-2H-1,4-benzothiazin-3(4H)-one prepared in Example 29, 14 g of ethyl 8-chloro-2H-1,4-benzothiazin-3-one-4-acetate are recovered in the form of an oil which can be used in the crude state for the next step.

EXAMPLE 60

Ethyl 7-chloro-2H-1,4-benzothiazin-3-one-4-acetate

Formula II: $R_1=7\text{-}Cl$; $R_2=R_3=R_4=H$; $X=CH$; $Y=S$; $Z=O$; $R'=C_2H_5$ Following the procedure of Example 52, but starting from 23 g of 7-chloro-2H-1,4-benzothiazin-3(4H)-one prepared in Example 30, 32 g of ethyl 7-chloro-2H-1,4-benzothiazin-3-one-4-acetate are obtained in the form of crystals of melting point 75°–78° C.

EXAMPLE 61

Ethyl 6-methoxy-2H-1,4-benzothiazin-3-one-4-acetate

Formula II: $R_1=6\text{-}OCH_3$; $R_2=R_3=R_4=H$; $X=CH$; $Y=S$; $Z=O$; $R'=C_2H_5$ Following the procedure of Example 52, but starting from 26.9 g of 6-methoxy-2H-1,4-benzothiazin-3(4H)-one prepared in Example 31, 24.5 g of ethyl 6-methoxy-2H-1,4-benzothiazin-3-one-4-acetate are obtained, after crystallization from ether, in the form of crystals of melting point 84°–87° C.

EXAMPLE 62

Ethyl 6-trifluoromethyl-7-chloro-2H-1,4-benzothiazin-3-one-4-acetate

Formula II: $R_1=6\text{-}CF_3$; $R_2=7\text{-}Cl$; $R_3=R_4=H$; $X=CH$; $Y=S$; $Z=O$; $R'=C_2H_5$ Following the procedure of Example 52, but starting from 15.5 g of 6-trifluoromethyl-7-chloro-2H-1,4-benzothiazin-3(4H)-one prepared in Example 32, 13 g of ethyl 6-trifluoromethyl-7-chloro-2H-1,4-benzothiazin-3-one-4-acetate are obtained, after crystallization from pentane, in the form of crystals of melting point 93° C.

EXAMPLE 63

Ethyl 2H-1,4-benzothiazin-3-one-4-acetate

Formula II: $R_1=R_2=R_3=R_4=H$; $X=CH$; $Y=S$; $Z=O$; $R'=C_2H_5$

Following the procedure of Example 52, but starting from 23 g of 2H-1,4-benzothiazin-3(4H)-one prepared in Example 33, 21.8 g of ethyl 2H-1,4-benzothiazin-3-one-4-acetate are obtained, after crystallization from isopropyl ether, in the form of crystals of melting point 43°–44° C.

EXAMPLE 64

Ethyl 2-methyl-2H-1,4-benzothiazin-3-one-4-acetate

Formula II: $R_1=R_2=R_3=H$; $R_4=CH_3$; $X=CH$; $Y=S$; $Z=O$; $R'=C_2H_5$

Following the procedure of Example 52, but starting from 34 g of 2-methyl-2H-1,4-benzothiazin-3(4H)-one prepared in Example 34, 39.6 g of ethyl 2-methyl-2H-1,4-benzothiazin-3-one-4-acetate are obtained, after crystallization from pentane, in the form of crystals of melting point 70°–72° C.

EXAMPLE 65

Ethyl 2-phenyl-2H-1,4-benzothiazin-3-one-4-acetate

Formula II: $R_1=R_2=R_3=H$; $R_4=$ phenyl; $X=CH$; $Y=S$; $Z=O$; $R'=C_2H_5$

Following the procedure of Example 52, but starting from 45.5 g of 2-phenyl-2H-1,4-benzothiazin-3(4H)-one prepared in Example 35, 38 g of ethyl 2-phenyl-2H-1,4-benzothiazin-3-one-4-acetate are obtained in the form of an oil which can be used in the crude state for the next step.

EXAMPLE 66

Ethyl 6-chloro-2H-1,4-benzothiazin-3-one-4-acetate

Formula II: $R_1=$6-Cl; $R_2=R_3=R_4=H$; $X=CH$; $Y=S$; $Z=O$; $R'=C_2H_5$

Following the procedure of Example 52, but starting from 27.3 g of 6-chloro-2H-1,4-benzothiazin-3(4H)-one prepared in Example 36, 32 g of ethyl 6-chloro-2H-1,4-benzothiazin-3-one-4-acetate are recovered, after recrystallization from pentane, in the form of crystals of melting point 72° C.

EXAMPLE 67

Ethyl 6-fluoro-2-methyl-2H-1,4-benzothiazin-3-one-4-acetate

Formula II: $R_1=$6-F; $R_3=CH_3$; $R_2=R_4=H$; $X=CH$; $Y=S$; $Z=O$; $R'=C_2H_5$ Following the procedure of Example 52, but starting from 20 g of 6-fluoro-2-methyl-2H-1,4-benzothiazin-3(4H)-one prepared in Example 37, 13 g of ethyl 6-fluoro-2-methyl-2H-1,4-benzothiazin-3-one-4-acetate are obtained, after crystallization from an isopropyl ether/pentane mixture, in the form of crystals of melting point 92° C.

EXAMPLE 68

Ethyl 6-chloro-2-methyl-2H-1,4-benzothiazin-3-one-4-acetate

Formula II: $R_1=$6-Cl; $R_3=CH_3$; $R_2=R_4=H$; $X=CH$; $Y=S$; $Z=O$; $R'=C_2H_5$ Following the procedure of Example 52, but starting from 19 g of 6-chloro-2-methyl-2H-1,4-benzothiazin-3(4H)-one prepared in Example 38, 24 g of ethyl 6-chloro-2-methyl-2H-1,4-benzothiazin-3-one-4-acetate are recovered, after crystallization from an isopropyl ether/pentane mixture, in the form of crystals of melting point 105° C.

EXAMPLE 69

Ethyl 6-chloro-2-phenyl-2H-1,4-benzothiazin-3-one-4-acetate

Formula II: $R_1=$6-Cl; $R_3=$ phenyl; $R_2=R_4=H$; $X=CH$; $Y=S$; $Z=O$; $R'=C_2H_5$ Following the procedure of Example 52, but starting from 6.3 g of 6-chloro-2-phenyl-2H-1,4-benzothiazin-3(4H)-one prepared in Example 39, 8 g of ethyl 6-chloro-2-phenyl-2H-1,4-benzothiazin-3-one-4-acetate are recovered in the form of an oil which can be used in the crude state for the next step.

EXAMPLE 70

Ethyl 2,2-dimethyl-2H-1,4-benzothiazin-3-one-4-acetate

Formula II: $R_1=R_2=H$; $R_3=R_4=CH_3$; $X=CH$; $Y=S$; $Z=O$; $R'=C_2H_5$

Following the procedure of Example 52, but starting from 40 g of 2,2-dimethyl-2H-1,4-benzothiazin-3(4H)-one prepared in Example 40, 50.1 g of ethyl 2,2-dimethyl-2H-1,4-benzothiazin-3-one-4-acetate are recovered, after crystallization from pentane, in the form of crystals of melting point 60° C.

EXAMPLE 71

Ethyl 2-parachlorophenyl-2H-1,4-benzothiazin-3-one-4-acetate

Formula II: $R_1=R_2=R_3=H$; $R_4=$ parachlorophenyl; $X=CH$; $Y=S$; $Z=O$; $R'=CH_2H_5$ Following the procedure of Example 52, but starting from 37.8 g of 2-parachlorophenyl-2H-1,4-benzothiazin-3(4H)-one prepared in Example 41, 25 g of ethyl 2-parachlorophenyl-2H-1,4-benzothiazin-3-one-4-acetate are obtained, after crystallization from an isopropyl ether/pentane/isopropanol mixture, in the form of crystals of melting point 118° C.

EXAMPLE 72

Ethyl 2-orthochlorophenyl-2H-1,4-benzothiazin-3-one-4-acetate

Formula II: $R_1=R_2=R_3=H$; $R_4=$ orthochlorophenyl; $X=CH$; $Y=S$; $Z=O$; $R'=C_2H_5$ Following the procedure of Example 52, but starting from 37 g of 2-orthochlorophenyl-2H-1,4-benzothiazin-3(4H)-one prepared in Example 42, 44.3 g of ethyl 2-orthochlorophenyl-2H-1,4-benzothiazin-3-one-4-acetate are obtained in the form of an oil which can be used in the crude state for the next step.

EXAMPLE 73

Ethyl 6,7-dichloro-2H-1,4-benzothiazin-3-one-4-acetate

Formula II: $R_1=$6-Cl; $R_2=$7-Cl; $R_3=R_4=H$; $X=CH$; $Y=S$; $Z=O$; $R'=C_2H_5$ Following the procedure of Example 52, but starting from 4.5 g of 6,7-dichloro-2H-1,4-benzothiazin-3(4H)-one prepared in Example 42, 4 g of ethyl 6,7-dichloro-2H-1,4-benzothiazin-3-one-4-acetate are obtained, after crystallization from isopropyl ether, in the form of crystals of melting point 160° C.

EXAMPLE 74

Ethyl 2-methyl-2-(pyridin-2'-yl)-2H-1,4-benzothiazin-3-one-4-acetate

Formula II: $R_1=R_2=H$; $R_3=CH_3$; $R_4=$ pyridin-2'-yl; $X=CH$; $Y=S$; $Z=O$; $R'=C_2H_5$ Following the procedure of Example 52, but starting from 9.5 g of 2-methyl-2-(pyridin-2'-yl)-2H-1,4-benzothiazin-3(4H)-one prepared in Example 44, 12 g of ethyl 2-methyl-2-(pyridin-2'-yl)-2H-1,4-benzothiazin-3-one-4-acetate are obtained in the form of an oil which can be used in the crude state for the next step.

EXAMPLE 75

Ethyl 6-fluoro-2H-1,4-benzoxazin-3-one-4-acetate

Formula II: $R_1=6\text{-}F$; $R_2=R_3=R_4=H$; $X=CH$; $Y=Z=O$; $R'=C_2H_5$

Following the procedure of Example 52, but starting from 27.3 g of 6-fluoro-2H-1,4-benzoxazin-3(4H)-one prepared in Example 45, 32 g of ethyl 6-fluoro-2H-1,4-benzoxazin-3-one-4-acetate are recovered in the form of crystals of melting point 73° C.

EXAMPLE 76

Ethyl 6-fluoro-3,4-dihydrocarbostyril-1-acetate

Formula II: $R_1=6\text{-}F$; $R_2=R_3=R_4=H$; $X=CH$; $Y=CH_2$; $Z=O$; $R'=C_2H_5$ Following the procedure of Example 52, but starting from 12.8 g of 6-fluoro-3,4-dihydrocarbostyril prepared in Example 46, 12.5 g of ethyl 6-fluoro-3,4-dihydrocarbostyril-1-acetate are recovered, after crystallization from an ether/pentane mixture, in the form of crystals of melting point 82°–86° C.

EXAMPLE 77

Ethyl 6-chloro-3,4-dihydrocarbostyril-1-acetate

Formula II: $R_1=6\text{-}Cl$; $R_2=R_3=R_4=H$; $X=CH$; $Y=CH_2$; $Z=O$; $R'=C_2H_5$ Following the procedure of Example 52, but starting from 33 g of 6-chloro-3,4-dihydrocarbostyril prepared in Example 47, 30.7 g of ethyl 6-chloro-3,4-dihydrocarbostyril-1-acetate are recovered, after crystallization from an ether/pentane mixture, in the form of crystals of melting point 72°–75° C.

EXAMPLE 78

Ethyl 7-fluoro-3,4-dihydrocarbostyril-1-acetate

Formula II: $R_1=7\text{-}F$; $R_2=R_3=R_4=H$; $X=CH$; $Y=CH_2$; $Z=O$; $R'=C_2H_5$ Following the procedure of Example 52, but starting from 30.8 g of 7-fluoro-3,4-dihydrocarbostyril prepared in Example 48, 36.3 g of ethyl 7-fluoro-3,4-dihydrocarbostyril-1-acetate are recovered, after crystallization from pentane, in the form of crystals of melting point 75°–78° C.

EXAMPLE 79

Ethyl 7-chloro-3,4-dihydrocarbostyril-1-acetate

Formula II: $R_1=7\text{-}Cl$; $R_2=R_3=R_4=H$; $X=CH$; $Y=CH_2$; $Z=O$; $R'=C_2H_5$ Following the procedure of Example 52, but starting from 40 g of 7-chloro-3,4-dihydrocarbostyril prepared in Example 49, 39.8 g of ethyl 7-chloro-3,4-dihydrocarbostyril-1-acetate are recovered, after crystallization from an ether/pentane mixture, in the form of crystals of melting point 79°–83° C.

EXAMPLE 80

Ethyl 2-parafluorophenyl-2H-1,4-benzothiazin-3-one-4-acetate

Formula II: $R_1=R_2=R_3=H$; $R_4=\text{parafluorophenyl}$; $X=CH$; $Y=S$; $Z=O$; $R'=C_2H_5$ Following the procedure of Example 52, but starting from 34.7 g of 2-parafluorophenyl-2H-1,4-benzothiazin-3(4H)-one prepared in Example 50, 35 g of ethyl 2-parafluorophenyl-2H-1,4-benzothiazin-3-one-4-acetate are obtained in the form of an oil which can be used in the crude state for the next step.

EXAMPLE 81

Ethyl 2-orthofluorophenyl-2H-1,4-benzothiazin-3-one-4-acetate

Formula II: $R_1=R_2=R_3=H$; $R_4=\text{orthofluorophenyl}$; $X=CH$; $Y=S$; $Z=O$; $R'=C_2H_5$ Following the procedure of Example 52, but starting from 33 g of 2-orthofluorophenyl-2H-1,4-benzothiazin-3(4H)-one prepared in Example 51, 37.4 g of ethyl 2-orthofluorophenyl-2H-1,4-benzothiazin-3-one-4-acetate are obtained in the form of crystals of melting point 118° C.

EXAMPLE 82

7-Chloro-2-methyl-2H-1,4-benzothiazin-3(4H)-one

Formula III: $R_1=7\text{-}Cl$; $R_3=CH_3$; $R_2=R_4=H$; $X=CH$; $Y=S$

Following the procedure of Example 28, but using 72 g of ethyl 5-chloro-2-nitrophenylthio-α-methylacetate prepared in Example 21, 26.8 g of 7-chloro-2-methyl-2H-1,4-benzothiazin-3(4H)-one are obtained in the form of crystals of melting point 200° C.

EXAMPLE 83

Ethyl 7-chloro-2-methyl-2H-1,4-benzothiazin-3-one-4-acetate

Formula II: $R_1=7\text{-}Cl$; $R_3=CH_3$; $R_2=R_4=H$; $X=CH$; $Y=S$; $Z=O$; $R'=C_2H_5$ Following the procedure of Example 52, but starting from 19.7 g of 7-chloro-2-methyl-2H-1,4-benzothiazin-3(4H)-one prepared in Example 82, 20.7 g of ethyl 7-chloro-2-methyl-2H-1,4-benzothiazin-3-one-4-acetate are obtained, after crystallization from ether, in the form of crystals of melting point 112°–113° C.

EXAMPLE 84

Ethyl 7-fluoro-2H-1,4-benzothiazine-3-thione-4-acetate

Formula II: $R_1=7\text{-}F$; $R_2=R_3=R_4=H$; $X=CH$; $Y=Z=S$; $R'=C_2H_5$

A solution of 19 g of ethyl 7-fluoro-2H-1,4-benzothiazin-3-one-4-acetate, prepared in Example 57, in 200 ml of chloroform containing 19 g of $P_2S_5$ is stirred for 15 hours at ambient temperature. The solution is subsequently filtered and then concentrated in vacuo and the residue is filtered on silica gel. By elution with benzene followed by recrystallization of the resulting crystals from hexane, 11.2 g of ethyl 7-fluoro-2H-1,4-benzothiazine-3-thione-4-acetate are obtained in the form of crystals of melting point 87° C.

EXAMPLE 85

Ethyl 6-fluoro-2H-1,4-benzothiazine-3-thione-4-acetate

Formula II: $R_1=6\text{-}F$; $R_2=R_3=R_4=H$; $X=CH$; $Y=Z=S$; $R'=C_2H_5$

Following the procedure of Example 84, but starting from 15 g of ethyl 6-fluoro-2H-1,4-benzothiazin-3-one-4-acetate prepared in Example 58, 7.4 g of ethyl 6-fluoro-2H-1,4-benzothiazine-3-thione-4-acetate are obtained, after filtration on silica gel, elution with benzene and crystallization from an isopropyl ether/pentane mixture, in the form of crystals of melting point 66° C.

EXAMPLE 86

Ethyl 7-chloro-2H-1,4-benzothiazine-3-thione-4-acetate

Formula II: $R_1=$7-Cl; $R_2=R_3=R_4=$H; $X=$CH; $Y=Z=$S; $R'=C_2H_5$

Following the procedure of Example 84, but starting from 32 g of ethyl 7-chloro-2H-1,4-benzothiazin-3-one-4-acetate prepared in Example 60, 20.5 g of ethyl 7-chloro-2H-1,4-benzothiazine-3-thione-4-acetate are recovered, after crystallization from pentane, in the form of crystals of melting point 98° C.

EXAMPLE 87

Ethyl 6-methoxy-2H-1,4-benzothiazine-3-thione-4-acetate

Formula II: $R_1=$6-OCH$_3$; $R_2=R_3=R_4=$H; $X=$CH; $Y=Z=$S; $R'=C_2H_5$

Following the procedure of Example 84, but starting from 12 g of ethyl 6-methoxy-2H-1,4-benzothiazin-3-one-4-acetate prepared in Example 61, 8 g of ethyl 6-methoxy-2H-1,4-benzothiazine-3-thione-4-acetate are recovered.

EXAMPLE 88

Ethyl 6-trifluoromethyl-7-chloro-2H-1,4-benzothiazine-3-thione-4-acetate

Formula II: $R_1=$6-CF$_3$; $R_2=$7-Cl; $R_3=R_4=$H; $X=$CH; $Y=Z=$S; $R'=C_2H_5$ Following the procedure of Example 84, but starting from 13 g of ethyl 6-trifluoromethyl-7-chloro-2H-1,4-benzothiazin-3-one-4-acetate prepared in Example 62, 5.1 g of ethyl 6-trifluoromethyl-7-chloro-2H-1,4-benzothiazine-3-thione-4-acetate are recovered, after crystallization from pentane, in the form of crystals of melting point 83° C.

EXAMPLE 89

Ethyl 2-phenyl-2H-1,4-benzothiazine-3-thione-4-acetate

Formula II: $R_1=R_2=R_3=$H; $R_4=$phenyl; $X=$CH; $Y=Z=$S; $R'=C_2H_5$

Following the procedure of Example 84, but starting from 23 g of ethyl 2-phenyl-2H-1,4-benzothiazin-3-one-4-acetate prepared in Example 65, 9 g of ethyl 2-phenyl-2H-1,4-benzothiazine-3-thione-4-acetate are recovered in the form of crystals of melting point 135° C.

EXAMPLE 90

Ethyl 6-trifluoromethyl-2H-1,4-benzothiazine-3-thione-4-acetate

Formula II: $R_1=$6-CF$_3$; $R_2=R_3=R_4=$H; $X=$CH; $Y=Z=$S; $R'=C_2H_5$

Following the procedure of Example 84, but starting from 31 g of ethyl 6-trifluoromethyl-2H-1,4-benzothiazin-3-one-4-acetate prepared in Example 56, 14 g of ethyl 6-trifluoromethyl-2H-1,4-benzothiazine-3-thione-4-acetate are obtained, after recrystallization from isopropanol, in the form of crystals of melting point 110° C.

EXAMPLE 91

Ethyl 2-methyl-2H-1,4-benzothiazine-3-thione-4-acetate

Formula II: $R_1=R_2=R_3=$H; $R_4=$CH$_3$; $X=$CH; $Y=Z=$S; $R'=C_2H_5$

A solution of 20 g of ethyl 2-methyl-2H-1,4-benzothiazin-3-one-4-acetate, prepared in Example 64, in 100 ml of dimethoxyethane is heated at 80° C. for 5 hours in the presence of 20 g of Lawesson's reagent. The reaction mixture is then concentrated in vacuo, the residue is taken up with 400 ml of hot cyclohexane and, after filtration, the cyclohexane is evaporated off in vacuo and the residue obtained is filtered on silica gel. By elution with toluene, 11 g of ethyl 2-methyl-2H-1,4-benzothiazine-3-thione-4-acetate are recovered in the form of crystals of melting point 65° C.

EXAMPLE 92

Ethyl 2H-1,4-benzothiazine-3-thione-4-acetate

Formula II: $R_1=R_2=R_3=R_4=$H; $X=$CH; $Y=Z=$S; $R'=C_2H_5$

Following the procedure of Example 84, but starting from 35 g of ethyl 2H-1,4-benzothiazin-3-one-4-acetate prepared in Example 63, 21 g of ethyl 2H-1,4-benzothiazine-3-thione-4-acetate are obtained, after crystallization from a pentane/isopropyl ether mixture, in the form of crystals of melting point 50° C.

EXAMPLE 93

Ethyl 6-chloro-2H-1,4-benzothiazine-3-thione-4-acetate

Formula II: $R_1=$6-Cl; $R_2=R_3=R_4=$H; $X=$CH; $Y=Z=$S; $R'=C_2H_5$

Following the procedure of Example 84, but starting from 23 g of ethyl 6-chloro-2H-1,4-benzothiazin-3-one-4-acetate prepared in Example 66, 11.5 g of ethyl 6-chloro-2H-1,4-benzothiazine-3-thione-4-acetate are obtained, after crystallization from an isopropyl ether/pentane mixture, in the form of crystals of melting point 64° C.

EXAMPLE 94

Ethyl 6-fluoro-2-methyl-2H-1,4-benzothiazine-3-thione-4-acetate

Formula II: $R_1=$6-F; $R_3=$CH$_3$; $R_2=R_4=$H; $X=$CH; $Y=Z=$S; $R'=C_2H_5$

Following the procedure of Example 84, but starting from 11 g of ethyl 6-fluoro-2-methyl-2H-1,4-benzothiazin-3-one-4-acetate prepared in Example 67, 6 g of ethyl 6-fluoro-2-methyl-2H-1,4-benzothiazine-3-thione-4-acetate are obtained in the form of crystals of melting point 91° C.

EXAMPLE 95

Ethyl 6-chloro-2-methyl-2H-1,4-benzothiazine-3-thione-4-acetate

Formula II: $R_1=$6-Cl; $R_3=$CH$_3$; $R_2=R_4=$H; $X=$CH; $Y=Z=$S; $R'=C_2H_5$

Following the procedure of Example 84, but starting from 17 g of ethyl 6-chloro-2-methyl-2H-1,4-benzothiazin-3-one-4-acetate prepared in Example 68, 9.5 g of ethyl 6-chloro-2-methyl-2H-1,4-benzothiazine-3-thione-4-acetate are obtained, after crystallization from pentane, in the form of crystals of melting point 55° C.

EXAMPLE 96

Ethyl 6-chloro-2-phenyl-2H-1,4-benzothiazine-3-thione-4-acetate

Formula II: $R_1=6\text{-}Cl$; $R_3=$phenyl; $R_2=R_4=H$; $X=CH$; $Y=Z=S$; $R'=C_2H_5$ Following the procedure of Example 84, but starting from 21 g of ethyl 6-chloro-2-phenyl-2H-1,4-benzothiazin-3-one-4-acetate prepared in Example 69, 11 g of ethyl 6-chloro-2-phenyl-2H-1,4-benzothiazine-3-thione-4-acetate are obtained, after crystallization from ether, in the form of crystals of melting point 148° C.

EXAMPLE 97

Ethyl 2,2-dimethyl-2H-1,4-benzothiazine-3-thione-4-acetate

Formula II: $R_1=R_2=H$; $R_3=R_4=CH_3$; $X=CH$; $Y=Z=S$; $R'=C_2H_5$

Following the procedure of Example 84, but starting from 25 g of ethyl 2,2-dimethyl-2H-1,4-benzothiazin-3-one-4-acetate prepared in Example 70, 11.2 g of ethyl 2,2-dimethyl-2H-1,4-benzothiazine-3-thione-4-acetate are obtained, after crystallization from pentane, in the form of crystals of melting point 82°–86° C.

EXAMPLE 98

Ethyl 2-parachlorophenyl-2H-1,4-benzothiazine-3-thione-4-acetate

Formula II: $R_1=R_2=R_3=H$; $R_4=$parachlorophenyl; $X=CH$; $Y=Z=S$; $R'=C_2H_5$ Following the procedure of Example 84, but starting from 17.5 g of ethyl 2-parachlorophenyl-2H-1,4-benzothiazin-3-one-4-acetate prepared in Example 71, 11.2 g of ethyl 2-parachlorophenyl-2H-1,4-benzothiazine-3-thione-4-acetate are obtained, after crystallization from an isopropyl ether/pentane mixture, in the form of crystals of melting point 94° C.

EXAMPLE 99

Ethyl 6,7-dichloro-2H-1,4-benzothiazine-3-thione-4-acetate

Formula II: $R_1=6\text{-}Cl$; $R_2=7\text{-}Cl$; $R_3=R_4=H$; $X=CH$; $Y=Z=S$; $R'=C_2H_5$ Following the procedurre of Example 84, but starting from 4 g of ethyl 6,7-dichloro-2H-1,4-benzothiazin-3-one-4-acetate prepared in Example 73, 2.4 g of ethyl 6,7-dichloro-2H-1,4-benzothiazine-3-thione-4-acetate are obtained, after crystallization from pentane, in the form of crystals of melting point 123° C.

EXAMPLE 100

Ethyl 7-chloro-2-methyl-2H-1,4-benzothiazine-3-thione-4-acetate

Formula II: $R_1=Cl$; $R_3=CH_3$; $R_2=R_4=H$; $X=CH$; $Y=Z=S$; $R'=C_2H_5$

Following the procedure of Example 84, but starting from 11.5 g of ethyl 7-chloro-2-methyl-2H-1,4-benzothiazin-3-one-4-acetate prepared in Example 83, 9.2 g of ethyl 7-chloro-2-methyl-2H-1,4-benzothiazine-3-thione-4-acetate are obtained.

EXAMPLE 101

Ethyl 2-orthochlorophenyl-2H-1,4-benzothiazine-3-thione-4-acetate

Formula II: $R_1=R_2=R_3=H$; $R_4=$orthochlorophenyl; $X=CH$; $Y=Z=S$; $R'=C_2H_5$ Following the procedure of Example 84, but starting from 32 g of ethyl 2-orthochlorophenyl-2H-1,4-benzothiazin-3-one-4-acetate prepared in Example 72, 18 g of ethyl 2-orthochlorophenyl-2H-1,4-benzothiazine-3-thione-4-acetate are obtained, after recrystallization from acetonitrile, in the form of crystals of melting point 154° C.

EXAMPLE 102

Ethyl 6-fluoro-2H-1,4-benzoxazine-3-thione-4-acetate

Formula II: $R_1=6\text{-}F$; $R_2=R_3=R_4=H$; $X=CH$; $Y=O$; $Z=S$; $R'=C_2H_5$ Following the procedure of Example 84, but starting from 22 g of ethyl 6-fluoro-2H-1,4-benzoxazin-3-one-4-acetate prepared in Example 75, 13.8 g of ethyl 6-fluoro-2H-1,4-benzoxazine-3-thione-4-acetate are obtained, after crystallization from an ether/pentane mixture, in the form of crystals of melting point 52° C.

EXAMPLE 103

Ethyl 6-fluoro-3,4-dihydroquinoline-2-thione-1-acetate

Formula II: $R_1=6\text{-}F$; $R_2=R_3=R_4=H$; $X=CH$; $Y=CH_2$; $Z=S$; $R'=C_2H_5$ Following the procedure of Example 84, but starting from 17 g of ethyl 6-fluoro-3,4-dihydrocarbostyril-1-acetate prepared in Example 76, 6.5 g of ethyl 6-fluoro-3,4-dihydroquinoline-2-thione-1-acetate are recovered in the form of crystals of melting point 80°–82° C.

EXAMPLE 104

Ethyl 6-chloro-3,4-dihydroquinoline-2-thione-1-acetate

Formula II: $R_1=6\text{-}Cl$; $R_2=R_3=R_4=H$; $X=CH$; $Y=CH_2$; $Z=S$; $R'=C_2H_5$ Following the procedure of Example 84, but starting from 20 g of ethyl 6-chloro-3,4-dihydrocarbostyril-1-acetate prepared in Example 77, 9.4 g of ethyl 6-chloro-3,4-dihydroquinoline-2-thione-1-acetate are recovered in the form of crystals of melting point 84°–87° C.

EXAMPLE 105

Ethyl 7-fluoro-3,4-dihydroquinoline-2-thione-1-acetate

Formula II: $R_1=7\text{-}F$; $R_2=R_3=R_4=H$; $X=CH$; $Y=CH_2$; $Z=S$; $R'=C_2H_5$ Following the procedure of Example 84, but starting from 26 g of ethyl 7-fluoro-3,4-dihydrocarbostyril-1-acetate prepared in Example 78, 15.7 g of ethyl 7-fluoro-3,4-dihydroquinoline-2-thione-1-acetate are recovered in the form of crystals of melting point 76°–79° C.

EXAMPLE 106

Ethyl 7-chloro-3,4-dihydroquinoline-2-thione-1-acetate

Formula II: $R_1=$7-Cl; $R_2=R_3=R_4=$H; $X=$CH; $Y=$CH$_2$; $Z=$S; $R'=$C$_2$H$_5$ Following the procedure of Example 84, but starting from 25.5 g of ethyl 7-chloro-3,4-dihydrocarbostyril-1-acetate prepared in Example 79, 12 g of ethyl 7-chloro-3,4-dihydroquinoline-2-thione-1-acetate are recovered in the form of crystals of melting point 68°–72° C.

EXAMPLE 107

Ethyl 3-methylpyrido[2,3-b][1,4]thiazine-2(3H)-thione-1-acetate

Formula II: $R_1=R_2=R_3=$H; $R_4=$CH$_3$; $X=$N; $Y=Z=$S; $R'=$C$_2$H$_5$

Following the procedure of Example 84, but starting from 10 g of ethyl 3-methylpyrido[2,3-b][1,4]thiazin-2(3H)-one-1-acetate prepared in Example 54, 3 g of ethyl 3-methylpyrido[2,3-b][1,4]thiazine-2(3H)-thione-1-acetate are recovered in the form of crystals of melting point 100° C.

EXAMPLE 108

Ethyl 2-parafluorophenyl-2H-1,4-benzothiazine-3-thione-4-acetate

Formula II: $R_1=R_2=R_3=$H; $R_4=$parafluorophenyl; $X=$CH; $Y=Z=$S; $R'=$C$_2$H$_5$ Following the procedure of Example 84, but starting from 23 g of ethyl 2-parafluorophenyl-2H-1,4-benzothiazin-3-one-4-acetate prepared in Example 80, 17 g of ethyl 2-parafluorophenyl-2H-1,4-benzothiazine-3-thione-4-acetate are recovered.

EXAMPLE 109

Ethyl 2-orthofluorophenyl-2H-1,4-benzothiazine-3-thione-4-acetate

Formula II: $R_1=R_2=R_3=$H; $R_4=$orthofluorophenyl; $X=$CH; $Y=Z=$S; $R'=$C$_2$H$_5$ Following the procedure of Example 84, but starting from 25 g of ethyl 2-orthofluorophenyl-2H-1,4-benzothiazin-3-one-4-acetate prepared in Example 81, 19 g of ethyl 2-orthofluorophenyl-2H-1,4-benzothiazine-3-thione-4-acetate are recovered in the form of crystals of melting point 174° C.

EXAMPLE 110

Pyrido[2,3-b]thiazin-2(3H)-one-1-acetic acid

Formula I: $R_1=R_2=R_3=R_4=$H; $X=$N; $Y=$S; $Z=$O

A solution of 9 g of ethyl pyrido[2,3-b]thiazin-2(3H)-one-1-acetate, prepared in Example 52, in 30 ml of methanol containing 1.5 g of sodium hydroxide dissolved in 20 ml of water is heated at 50° C. for 10 minutes. The reaction mixture is subsequently treated with active charcoal, then filtered and acidified in the cold with dilute hydrochloric acid, concentrated in vacuo to half its volume and then treated with water and ice. The crystals formed are filtered off, washed twice with 10 ml of water and then with acetone and dried. 5.5 g of pyrido[2,3-b]thiazin-2(3H)-one-1-acetic acid are thus recovered in the form of crystals of melting point 252°–255° C.

EXAMPLE 111

6-Chloropyrido[2,3-b]thiazin-2(3H)-one-1-acetic acid

Formula I: $R_1=$6-Cl; $R_2=R_3=R_4=$H; $X=$N; $Y=$S; $Z=$O

Following the procedure of Example 110, but using 3.5 g of ethyl 6-chloropyrido[2,3-b]thiazin-2(3H)-one-1-acetate prepared in Example 53, 2 g of 6-chloropyrido[2,3-b]thiazin-2(3H)-one-1-acetic acid are obtained in the form of crystals of melting point 195°–200° C.

EXAMPLE 112

3-Methylpyrido[2,3-b]thiazin-2(3H)-one-1-acetic acid

Formula I: $R_1=R_2=R_3=$H; $R_4=$CH$_3$; $X=$N; $Y=$S; $Z=$O

Following the procedure of Example 110, but using 7 g of ethyl 3-methylpyrido[2,3-b]thiazin-2(3H)-one-1-acetate prepared in Example 54, 3 g of 3-methylpyrido[2,3-b]thiazin-2(3H)-one-1-acetic acid are recovered in the form of crystals of melting point 189°–190° C.

EXAMPLE 113

3-Methylpyrido[2,3-b]thiazine-2(3H)-thione-1-acetic acid

Formula I: $R_1=R_2=R_3=$H; $R_4=$CH$_3$; $X=$N; $Y=Z=$S

A solution of 3 g of ethyl 3-methylpyrido[2,3-b][1,4]thiazine-2(3H)-thione-1-acetate, prepared in Example 107, in 25 ml of tetrahydrofuran and 25 ml of ethanol containing 0.5 g of sodium hydroxide dissolved in 10 ml of water is stirred for 24 hours. The mixture is subsequently concentrated in vacuo, without heating, and then, after the addition of water, the neutral components are extracted with ether. The aqueous phase is acidified in the cold with acetic acid and the organic products are extracted with chloroform. The chloroform phase is dried, the chloroform is evaporated off and the residue obtained crystallizes from ether. The crystals are filtered off, washed with a small quantity of ether and dried. 1 g of 3-methylpyrido[2,3-b]thiazine-2(3H)-thione-1-acetic acid is thus recovered in the form of crystals of melting point 196°–198° C.

EXAMPLE 114

Pyrido[2,3-b][1,4]pyrazin-2(3H)-one-1-acetic acid hydrochloride

Formula I: $R_1=R_2=R_3=R_4=$H; $X=Y=$N; $Z=$O

A solution of 7.8 g of ethyl pyrido[2,3-b][1,4]pyrazin-2(3H)-one-1-acetate hydrochloride, prepared in Example 55, in 50 ml of 3N hydrochloric acid is heated under refulx for 7 hours. The reaction mixture is then concentrated in vacuo and the residue is taken up in acetone, from which it crystallizes. The crystals are filtered off, washed with acetone, dried and recrystallized from acetic acid. 3.6 g of pyrido[2,3-b][1,4]pyrazin-2(3H)-one-1-acetic acid hydrochloride are thus obtained in the form of crystals of melting point 260°–265° C. with decomposition.

EXAMPLE 115

6-Trifluoromethyl-2H-1,4-benzothiazin-3-one-4-acetic acid

Formula I: $R_1=6\text{-}CF_3$; $R_2=R_3=R_4=H$; $X=CH$; $Y=S$; $Z=O$

A solution of 10.5 g of ethyl 6-trifluoromethyl-2H-1,4-benzothiazin-3-one-4-acetate, prepared in Example 56, in 20 ml of ethanol containing 2 g of sodium hydroxide dissolved in 10 ml of water is heated at 60° C. for 15 minutes. The reaction mixture is subsequently treated with active charcoal and then filtered and acidified in the cold with dilute hydrochloric acid. The crystals thus obtained are filtered off, washed with water and then with isopropyl ether and dried. 7 g of 6-trifluoromethyl-2H-1,4-benzothiazin-3-one-4-acetic acid are thus recovered in the form of crystals of melting point 165°–167° C.

EXAMPLE 116

7-Fluoro-2H-1,4-benzothiazin-3-one-4-acetic acid

Formula I: $R_1=7\text{-}F$; $R_2=R_3=R_4=H$; $X=CH$; $Y=S$; $Z=O$

Following the procedure of Example 115, but starting from 11 g of ethyl 7-fluoro-2H-1,4-benzothiazin-3-one-4-acetate prepared in Example 57, 7 g of 7-fluoro-2H-1,4-benzothiazin-3-one-4-acetic acid are recovered in the form of crystals of melting point 152°–154° C.

EXAMPLE 117

7-Fluoro-2H-1,4-benzothiazine-3-thione-4-acetic acid

Formula I: $R_1=7\text{-}F$; $R_2=R_3=R_4=H$; $X=CH$; $Y=Z=S$

A solution of 8.7 g of ethyl 7-fluoro-2H-1,4-benzothiazine-3-thione-4-acetate, prepared in Example 84, in 100 ml of methanol containing 1.2 g of sodium hydroxide dissolved in 15 ml of water is left to stand for 2 days at ambient temperature. The reaction mixture is subsequently concentrated in vacuo in the cold and then diluted with water and extracted with ether. The aqueous phase is then acidified in the cold with dilute hydrochloric acid and extracted with ether. This ether phase is washed with water and dried and then, after filtration, the ether is evaporated off in vacuo. The residue obtained crystallizes from an ether/hexane mixture. 6 g of 7-fluoro-2H-1,4-benzothiazine-3-thione-4-acetic acid are thus recovered, after filtration and drying, in the form of crystals of melting point 156°–157° C.

EXAMPLE 118

6-Fluoro-2H-1,4-benzothiazin-3-one-4-acetic acid

Formula I: $R_1=6\text{-}F$; $R_2=R_3=R_4=H$; $X=CH$; $Y=S$; $Z=O$

Following the procedure of Example 115, but starting from 12 g of ethyl 6-fluoro-2H-1,4-benzothiazin-3-one-4-acetate prepared in Example 58, 7.5 g of 6-fluoro-2H-1,4-benzothiazin-3-one-4-acetic acid are obtained, after crystallization from toluene, in the form of crystals of melting point 156°–157° C.

EXAMPLE 119

6-Fluoro-2H-1,4-benzothiazine-3-thione-4-acetic acid

Formula I: $R_1=6\text{-}F$; $R_2=R_3=R_4=H$; $X=CH$; $Y=Z=S$

Following the procedure of Example 117, but starting from 7.4 g of ethyl 6-fluoro-2H-1,4-benzothiazine-3-thione-4-acetate prepared in Example 85, 5.3 g of 6-fluoro-2H-1,4-benzothiazine-3-thione-4-acetic acid are obtained in the form of crystals of melting point 188°–190° C.

EXAMPLE 120

8-Chloro-2H-1,4-benzothiazin-3-one-4-acetic acid

Formula I: $R_1=8\text{-}Cl$; $R_2=R_3=R_4=H$; $X=CH$; $Y=S$; $Z=O$

Following the procedure of Example 115, but starting from 14 g of ethyl 8-chloro-2H-1,4-benzothiazin-3-one-4-acetate prepared in Example 59, 7.5 g of 8-chloro-2H-1,4-benzothiazin-3-one-4-acetic acid are obtained in the form of crystals of melting point 175°–177° C.

EXAMPLE 121

7-Chloro-2H-1,4-benzothiazin-3-one-4-acetic acid

Formula I: $R_1=7\text{-}Cl$; $R_2=R_3=R_4=H$; $X=CH$; $Y=S$; $Z=O$

Following the procedure of Example 115, but starting from 14.3 g of ethyl 7-chloro-2H-1,4-benzothiazin-3-one-4-acetate prepared in Example 60, 8.5 g of 7-chloro-2H-1,4-benzothiazin-3-one-4-acetic acid are recovered in the form of crystals of melting point 188°–190° C.

EXAMPLE 122

6-Methoxy-2H-1,4-benzothiazin-3-one-4-acetic acid

Formula I: $R_1=6\text{-}OCH_3$; $R_2=R_3=R_4=H$; $X=CH$; $Y=S$; $Z=O$

Following the procedure of Example 115, but starting from 17 g of ethyl 6-methoxy-2H-1,4-benzothiazin-3-one-4-acetate prepared in Example 61, 8.6 g of 6-methoxy-2H-1,4-benzothiazin-3-one-4-acetic acid are recovered, after recrystallization from acetonitrile, in the form of crystals of melting point 152°–155° C.

EXAMPLE 123

6-Trifluoromethyl-7-chloro-2H-1,4-benzothiazin-3-one-4-acetic acid

Formula I: $R_1=6\text{-}CF_3$; $R_2=7\text{-}Cl$; $R_3=R_4=H$; $X=CH$; $Y=S$; $Z=O$ Following the procedure of Example 115, but starting from 6 g of ethyl 6-trifluoromethyl-7-chloro-2H-1,4-benzothiazin-3-one-4-acetate prepared in Example 62, 4.3 g of 6-trifluoromethyl-7-chloro-2H-1,4-benzothiazin-3-one-4-acetic acid are recovered in the form of crystals of melting point 157°–159° C.

EXAMPLE 124

2H-1,4-Benzothiazin-3-one-4-acetic acid

Formula I: $R_1=R_2=R_3=R_4=H$; $X=CH$; $Y=S$; $Z=O$

Following the procedure of Example 115, but starting from 14 g of ethyl 2H-1,4-benzothiazin-3-one-4-acetate prepared in Example 63, 10 g of 2H-1,4-benzothiazin-3-one-4-acetic acid are recovered in the form of crystals of melting point 152°–154° C.

EXAMPLE 125

2-Methyl-2H-1,4-benzothiazin-3-one-4-acetic acid

Formula I: $R_1=R_2=R_3=H$; $R_4=CH_3$; $X=CH$; $Y=S$; $Z=O$

Following the procedure of Example 115, but starting from 13 g of ethyl 2-methyl-2H-1,4-benzothiazin-3-one-4-acetate prepared in Example 64, 8 g of 2-methyl-2H-1,4-benzothiazin-3-one-4-acetic acid are obtained in the form of crystals of melting point 113°–115° C.

EXAMPLE 126

2-Phenyl-2H-1,4-benzothiazin-3-one-4-acetic acid

Formula I: $R_1=R_2=R_3=H$; $R_4=$phenyl; $X=CH$; $Y=S$; $Z=O$

Following the procedure of Example 115, but starting from 15 g of ethyl 2-phenyl-2H-1,4-benzothiazin-3-one-4-acetate prepared in Example 65, 7.8 g of 2-phenyl-2H-1,4-benzothiazin-3-one-4-acetic acid are obtained in the form of crystals of melting point 155°–157° C.

EXAMPLE 127

7-Chloro-2H-1,4-benzothiazine-3-thione-4-acetic acid

Formula I: $R_1=7$-Cl; $R_2=R_3=R_4=H$; $X=CH$; $Y=Z=S$

Following the procedure of Example 117, but starting from 20.5 g of ethyl 7-chloro-2H-1,4-benzothiazine-3-thione-4-acetate prepared in Example 86, 8 g of 7-chloro-2H-1,4-benzothiazine-3-thione-4-acetic acid are obtained in the form of crystals of melting point 181°–183° C.

EXAMPLE 128

6-Methoxy-2H-1,4-benzothiazine-3-thione-4-acetic acid

Formula I: $R_1=6$-OCH$_3$; $R_2=R_3=R_4=H$; $X=CH$; $Y=Z=S$

Following the procedure of Example 117, but starting from 8 g of ethyl 6-methoxy-2H-1,4-benzothiazine-3-thione-4-acetate prepared in Example 87, 5.5 g of 6-methoxy-2H-1,4-benzothiazine-3-thione-4-acetic acid are recovered in the form of crystals of melting point 163°–165° C.

EXAMPLE 129

6-Trifluoromethyl-7-chloro-2H-1,4-benzothiazine-3-thione-4-acetic acid

Formula I: $R_1=6$-CF$_3$; $R_2=7$-Cl; $R_3=R_4=H$; $X=CH$; $Y=Z=S$

Following the procedure of Example 117, but starting from 5.1 g of ethyl 6-trifluoromethyl-7-chloro-2H-1,4-benzothiazine-3-thione-4-acetate prepared in Example 88, 3.5 g of 6-trifluoromethyl-7-chloro-2H-1,4-benzothiazine-3-thione-4-acetic acid are obtained in the form of crystals of melting point 170°–172° C.

EXAMPLE 130

2-Phenyl-2H-1,4-benzothiazine-3-thione-4-acetic acid

Formula I: $R_1=R_2=R_3=H$; $R_4=$phenyl; $X=CH$; $Y=Z=S$

Following the procedure of Example 117, but starting from 9 g of ethyl 2-phenyl-2H-1,4-benzothiazine-3-thione-4-acetate prepared in Example 89, 4.2 g of 2-phenyl-2H-1,4-benzothiazine-3-thione-4-acetic acid are obtained in the form of crystals of melting point 182°–184° C.

EXAMPLE 131

6-Trifluoromethyl-2H-1,4-benzothiazine-3-thione-4-acetic acid

Formula I: $R_1=6$-CF$_3$; $R_2=R_3=R_4=H$; $X=CH$; $Y=Z=S$

Following the procedure of Example 117, but starting from 14 g of ethyl 6-trifluoromethyl-2H-1,4-benzothiazine-3-thione-4-acetate prepared in Example 90, 5.5 g of 6-trifluoromethyl-2H-1,4-benzothiazine-3-thione-4-acetic acid are recovered in the form of crystals of melting point 163°–165° C.

EXAMPLE 132

2-Methyl-2H-1,4-benzothiazine-3-thione-4-acetic acid

Formula I: $R_1=R_2=R_3H$; $R_4=CH_3$; $X=CH$; $Y=Z=S$

Following the procedure of Example 117, but starting from 11 g of ethyl 2-methyl-2H-1,4-benzothiazine-3-thione-4-acetate prepared in Example 91, 4.5 g of 2-methyl-2H-1,4-benzothiazine-3-thione-4-acetic acid are obtained in the form of crystals of melting point 128°–131° C.

EXAMPLE 133

2H-1,4-Benzothiazine-3-thione-4-acetic acid

Formula I: $R_1=R_2=R_3=R_4=H$; $X=CH$; $Y=Z=S$

Following the procedure of Example 117, but starting from 21 g of ethyl 2H-1,4-benzothiazine-3-thione-4-acetate prepared in Example 92, 9 g of 2H-1,4-benzothiazine-3-thione-4-acetic acid are recovered in the form of crystals of melting point 187°–188° C.

EXAMPLE 134

6-Chloro-2H-1,4-benzothiazin-3-one-4-acetic acid

Formula I: $R_1=6$-Cl; $R_2=R_3=R_4=H$; $X=CH$; $Y=S$; $Z=O$

Following the procedure of Example 115, but starting from 9 g of ethyl 6-chloro-2H-1,4-benzothiazin-3-one-4-acetate prepared in Example 66, 5.5 g of 6-chloro-2H-1,4-benzothiazin-3-one-4-acetic acid are obtained in the form of crystals of melting point 151°–153° C.

EXAMPLE 135

6-Chloro-2H-1,4-benzothiazine-3-thione-4-acetic acid

Formula I: $R_1=6$-Cl; $R_2=R_3=R_4=H$; $X=CH$; $Y=Z=S$

Following the procedure of Example 117, but starting from 11 g of ethyl 6-chloro-2H-1,4-benzothiazine-3-thione-4-acetate prepared in Example 93, 5.2 g of 6-chloro-2H-1,4-benzothiazine-3-thione-4-acetic acid are recovered in the form of crystals of melting point 186°–188° C.

EXAMPLE 136

6-Fluoro-2-methyl-2H-1,4-benzothiazin-3-one-4-acetic acid

Formula I: $R_1=6$-F; $R_3=CH_3$; $R_2=R_4=H$; $X=CH$; $Y=S$; $Z=O$

Following the procedure of Example 115, but starting from 10 g of ethyl 6-fluoro-2-methyl-2H-1,4-benzothiazin-3-one-4-acetate prepared in Example 67, 6.5 g of 6-fluoro-2-methyl-2H-1,4-benzothiazin-3-one-4-acetic acid are recovered in the form of crystals of melting point 139°–141° C.

EXAMPLE 137

6-Fluoro-2-methyl-2H-1,4-benzothiazine-3-thione-4-acetic acid

Formula I: $R_1=6$-F; $R_3=CH_3$; $R_2=R_4=H$; $X=CH$; $Y=Z=S$

Following the procedure of Example 117, but starting from 6 g of ethyl 6-fluoro-2-methyl-2H-1,4-benzothiazine-3-thione-4-acetate prepared in Example 94, 3 g of 6-fluoro-2-methyl-2H-1,4-benzothiazine-3-thione-4-acetic acid are obtained in the form of crystals of melting point 138°–140° C.

EXAMPLE 138

6-Chloro-2-methyl-2H-1,4-benzothiazin-3-one-4-acetic acid

Formula I: $R_1=6$-Cl; $R_3=CH_3$; $R_2=R_4=H$; $X=CH$; $Y=S$; $Z=O$

Following the procedure of Example 115, but starting from 7 g of ethyl 6-chloro-2-methyl-2H-1,4-benzothiazin-3-one-4-acetate prepared in Example 68, 4.9 g of 6-chloro-2-methyl-2H-1,4-benzothiazin-3-one-4-acetic acid are obtained in the form of crystals of melting point 129°–131° C.

EXAMPLE 139

6-Chloro-2-phenyl-2H-1,4-benzothiazin-3-one-4-acetic acid

Formula I: $R_1=6$-Cl; $R_3=$phenyl; $R_2=R_4=H$; $X=CH$; $Y=S$; $Z=O$

Following the procedure of Example 115, but starting from 8 g of ethyl 6-chloro-2-phenyl-2H-1,4-benzothiazin-3-one-4-acetate prepared in Example 69, 5.3 g of 6-chloro-2-phenyl-2H-1,4-benzothiazin-3-one-4-acetic acid are recovered in the form of crystals of melting point 169°–170° C.

EXAMPLE 140

6-Chloro-2-methyl-2H-1,4-benzothiazine-3-thione-4-acetic acid

Formula I: $R_1=6$-Cl; $R_3=CH_3$; $R_2=R_4=H$; $X=CH$; $Y=Z=S$

Following the procedure of Example 117, but starting from 9 g of ethyl 6-chloro-2-methyl-2H-1,4-benzothiazine-3-thione-4-acetate prepared in Example 95, 4.5 g of 6-chloro-2-methyl-2H-1,4-benzothiazine-3-thione-4-acetic acid are recovered in the form of crystals of melting point 126°–128° C.

EXAMPLE 141

2,2-Dimethyl-2H-1,4-benzothiazin-3-one-4-acetic acid

Formula I: $R_1=R_2=H$; $R_3=R_4=CH_3$; $X=CH$; $Y=S$; $Z=O$

Following the procedure of Example 115, but starting from 15 g of ethyl 2,2-dimethyl-2H-1,4-benzothiazin-3-one-4-acetate prepared in Example 70, 12 g of 2,2-dimethyl-2H-1,4-benzothiazin-3-one-4-acetic acid are obtained in the form of crystals of melting point 114°–116° C.

EXAMPLE 142

6-Chloro-2-phenyl-2H-1,4-benzothiazine-3-thione-4-acetic acid

Formula I: $R_1=6$-Cl; $R_3=$phenyl; $R_2=R_4=H$; $X=CH$; $Y=Z=S$

Following the procedure of Example 117, but using 11 g of ethyl 6-chloro-2-phenyl-2H-1,4-benzothiazine-3-thione-4-acetate prepared in Example 96, 4.5 g of 6-chloro-2-phenyl-2H-1,4-benzothiazine-3-thione-4-acetic acid are recovered in the form of crystals of melting point 199°–201° C.

EXAMPLE 143

2-Parachlorophenyl-2H-1,4-benzothiazin-3-one-4-acetic acid

Formula I: $R_1=R_2=R_3=H$; $R_4=$parachlorophenyl; $X=CH$; $Y=S$; $Z=O$

Following the procedure of Example 115, but starting from 7 g of ethyl 2-parachlorophenyl-2H-1,4-benzothiazin-3-one-4-acetate prepared in Example 71, 5 g of 2-parachlorophenyl-2H-1,4-benzothiazin-3-one-4-acetic acid are recovered in the form of crystals of melting point 138°–140° C.

EXAMPLE 144

2-Orthochlorophenyl-2H-1,4-benzothiazin-3-one-4-acetic acid

Formula I: $R_1=R_2=R_3=H$; $R_4=$orthochlorophenyl; $X=CH$; $Y=S$; $Z=O$

Following the procedure of Example 115, but starting from 10 g of ethyl 2-orthochlorophenyl-2H-1,4-benzothiazin-3-one-4-acetate prepared in Example 72, 6.3 g of 2-orthochlorophenyl-2H-1,4-benzothiazin-3-one-4-acetic acid are obtained in the form of crystals of melting point 164°–165° C.

EXAMPLE 145

7-Chloro-2-methyl-2H-1,4-benzothiazin-3-one-4-acetic acid

Formula I: $R_1=7$-Cl; $R_3=CH_3$; $R_2=R_4=H$; $X=CH$; $Y=S$; $Z=O$

Following the procedure of Example 115, but starting from 7.2 g of ethyl 7-chloro-2-methyl-2H-1,4-benzothiazin-3-one-4-acetate prepared in Example 83, 3.2 g of 7-chloro-2-methyl-2H-1,4-benzothiazin-3-one-4-acetic acid are recovered in the form of crystals of melting point 117°–119° C.

EXAMPLE 146

2,2-Dimethyl-2H-1,4-benzothiazine-3-thione-4-acetic acid

Formula I: $R_1=R_2=H$; $R_3=R_4=CH_3$; $X=CH$; $Y=Z=S$

Following the procedure of Example 117, but starting from 11.2 g of ethyl 2,2-dimethyl-2H-1,4-benzothiazine-3-thione-4-acetate prepared in Example 97, 5.8 g of 2,2-dimethyl-2H-1,4-benzothiazine-3-thione-4-acetic acid are obtained in the form of crystals of melting point 176°–178° C.

EXAMPLE 147

2-Parachlorophenyl-2H-1,4-benzothiazine-3-thione-4-acetic acid

Formula I: $R_1=R_2=R_3=H$; $R_4=$ parachlorophenyl; $X=CH$; $Y=Z=S$

Following the procedure of Example 117, but starting from 11.2 g of ethyl 2-parachlorophenyl-2H-1,4-benzothiazine-3-thione-4-acetate prepared in Example 98, 5.9 g of 2-parachlorophenyl-2H-1,4-benzothiazine-3-thione-4-acetic acid are obtained in the form of crystals of melting point 173°–174° C.

EXAMPLE 148

2-Orthochlorophenyl-2H-1,4-benzothiazine-3-thione-4-acetic acid

Formula I: $R_1=R_2=R_3=H$; $R_4=$ orthochlorophenyl; $X=CH$; $Y=Z=S$

Following the procedure of Example 117, but starting from 18 g of ethyl 2-orthochlorophenyl-2H-1,4-benzothiazine-3-thione-4-acetate synthesized in Example 101, 8.2 g of 2-orthochlorophenyl-2H-1,4-benzothiazine-3-thione-4-acetic acid are recovered in the form of crystals of melting point 179°–181° C.

EXAMPLE 149

6,7-Dichloro-2H-1,4-benzothiazine-3-thione-4-acetic acid

Formula I: $R_1=6$-Cl; $R_2=7$-Cl; $R_3=R_4=H$; $X=CH$; $Y=Z=S$

Following the procedure of Example 117, but starting from 2.4 g of ethyl 6,7-dichloro-2H-1,4-benzothiazine-3-thione-4-acetate prepared in Example 99, 1 g of 6,7-dichloro-2H-1,4-benzothiazine-3-thione-4-acetic acid is obtained in the form of crystals of melting point 185°–187° C.

EXAMPLE 150

7-Chloro-2-methyl-2H-1,4-benzothiazine-3-thione-4-acetic acid

Formula I: $R_1=7$-Cl; $R_3=CH_3$; $R_2=R_4=H$; $X=CH$; $Y=Z=S$

Following the procedure of Example 117, but starting from 9.2 g of ethyl 7-chloro-2-methyl-2H-1,4-benzothiazine-3-thione-4-acetate prepared in Example 100, 5 g of 7-chloro-2-methyl-2H-1,4-benzothiazine-3-thione-4-acetic acid are obtained in the form of crystals of melting point 136°–138° C.

EXAMPLE 151

2-Methyl-2-(pyridin-2'-yl)-2H-1,4-benzothiazin-3-one-4-acetic acid

Formula I: $R_1=R_2=H$; $R_3=CH_3$; $R_4=$ pyridin-2'-yl; $X=CH$; $Y=S$; $Z=O$

Following the procedure of Example 115, but starting from 12 g of ethyl 2-methyl-2-(pyridin-2'-yl)-2H-1,4-benzothiazin-3-one-4-acetate prepared in Example 74 and neutralizing at the end of the saponification with acetic acid instead of hydrochloric acid, 5.6 g of 2-methyl-2-(pyridin-2'-yl)-2H-1,4-benzothiazin-3-one-4-acetic acid are obtained in the form of crystals of melting point 194°–196° C.

EXAMPLE 152

6-Fluoro-2H-1,4-benzoxazine-3-thione-4-acetic acid

Formula I: $R_1=6$-F; $R_2=R_3=R_4=H$; $X=CH$; $Y=O$; $Z=S$

Following the procedure of Example 117, but using 8.8 g of ethyl 6-fluoro-2H-1,4-benzoxazine-3-thione-4-acetate prepared in Example 102, 1.5 g of 6-fluoro-2H-1,4-benzoxazine-3-thione-4-acetic acid are obtained, after filtration on silica gel and elution with benzene, in the form of crystals of melting point 153°–155° C.

EXAMPLE 153

6-Fluoro-3,4-dihydroquinoline-2-thione-1-acetic acid

Formula I: $R_1=6$-F; $R_2=R_3=R_4=H$; $X=CH$; $Y=CH_2$; $Z=S$

Following the procedure of Example 117, but using 6.5 g of ethyl 6-fluoro-3,4-dihydroquinoline-2-thione-1-acetate prepared in Example 103, 2.9 g of 6-fluoro-3,4-dihydroquinoline-2-thione-1-acetic acid are obtained, after recrystallization from acetonitrile, in the form of crystals of melting point 177°–180° C.

EXAMPLE 154

6-Chloro-3,4-dihydroquinoline-2-thione-1-acetic acid

Formula I: $R_1=6$-Cl; $R_2=R_3=R_4=H$; $X=CH$; $Y=CH_2$; $Z=S$

Following the procedure of Example 117, but using 9.4 g of ethyl 6-chloro-3,4-dihydroquinoline-2-thione-1-acetate prepared in Example 104, 3.5 g of 6-chloro-3,4-dihydroquinoline-2-thione-1-acetic acid are recovered in the form of crystals of melting point 165° C.

EXAMPLE 155

7-Fluoro-3,4-dihydroquinoline-2-thione-1-acetic acid

Formula I: $R_1=7$-F; $R_2=R_3=R_4=H$; $X=CH$; $Y=CH_2$; $Z=S$

Following the procedure of Example 117, but using 15.7 g of ethyl 7-fluoro-3,4-dihydroquinoline-2-thione-1-acetate prepared in Example 105, 5.8 g of 7-fluoro-3,4-dihydroquinoline-2-thione-1-acetic acid are recovered in the form of crystals of melting point 154°–156° C.

EXAMPLE 156

7-Chloro-3,4-dihydroquinoline-2-thione-1-acetic acid

Formula I: $R_1=7$-Cl; $R_2=R_3=R_4=H$; $X=CH$; $Y=CH_2$; $Z=S$

Following the procedure of Example 117, but starting from 12 g of ethyl 7-chloro-3,4-dihydroquinoline-2- thione-1-acetate prepared in Example 106, 4 g of 7-chloro-3,4-dihydroquinoline-2-thione-1-acetic acid are recovered, after recrystallization from a toluene/acetonitrile mixture, in the form of crystals of melting point 148°–155° C.

EXAMPLE 157

2-Parafluorophenyl-2H-1,4-benzothiazin-3-one-4-acetic acid

Formula I: $R_1=R_2=R_3=H$; $R_4=$parafluorophenyl; $X=CH$; $Y=S$; $Z=O$

Following the procedure of Example 115, but starting from 12 g of ethyl 2-parafluorophenyl-2H-1,4-benzothiazin-3-one-4-acetate prepared in Example 80, 7 g of 2-parafluorophenyl-2H-1,4-benzothiazin-3-one-4-acetic acid are recovered in the form of crystals of melting point 140°–141° C.

EXAMPLE 158

2-Orthofluorophenyl-2H-1,4-benzothiazin-3-one-4-acetic acid

Formula I: $R_1=R_2=R_3=H$; $R_4=$orthofluorophenyl; $X=CH$; $Y=S$; $Z=O$

Following the procedure of Example 115, but starting from 12 g of ethyl 2-orthofluorophenyl-2H-1,4-benzothiazin-3-one-4-acetate prepared in Example 81, 10.2 g of 2-orthofluorophenyl-2H-1,4-benzothiazin-3-one-4-acetic acid are obtained in the form of crystals of melting point 162°–163° C.

EXAMPLE 159

2-Parafluorophenyl-2H-1,4-benzothiazine-3-thione-4-acetic acid

Formula I: $R_1=R_2=R_3=H$; $R_4=$parafluorophenyl; $X=CH$; $Y=Z=S$

Following the procedure of Example 117, but starting from 12 g of ethyl 2-parafluorophenyl-2H-1,4-benzothiazine-3-thione-4-acetate prepared in Example 108, 4.2 g of 2-parafluorophenyl-2H-1,4-benzothiazine-3-thione-4-acetic acid are obtained, after crystallization from an isopropyl ether/pentane mixture, in the form of crystals of melting point 160°–161° C.

EXAMPLE 160

2-Orthofluorophenyl-2H-1,4-benzothiazine-3-thione-4-acetic acid

Formula I: $R_1=R_2=R_3=H$; $R_4=$orthofluorophenyl; $X=CH$; $Y=Z=S$

Following the procedure of Example 117, but starting from 19 g of ethyl 2-orthofluorophenyl-2H-1,4-benzothiazine-3-thione-4-acetate obtained in Example 109, 7 g of 2-orthofluorophenyl-2H-1,4-benzothiazine-3-thione-4-acetic acid are recovered, after crystallization from an isopropyl ether/pentane mixture, in the form of crystals of melting point 180°–182° C.

EXAMPLE 161

4-Fluoro-2-nitrophenylthio-α,α'-dimethylacetic acid

Formula VIII: $R_1=4$-F; $R_3=R_4=CH_3$; $R_2=H$; $X=CH$; $Y=S$; $R''=H$

Following the procedure of Example 1, but using 48 g of 2,5-difluoronitrobenzene and 36.2 g of α-mercaptoisobutyric acid, 37.4 g of 4-fluoro-2-nitrophenyl-α,α'-dimethylacetic acid are obtained, after acidification with acetic acid, extraction with ether and crystallization of the residue from an isopropyl ether/pentane mixture, in the form of crystals of melting point 104° C.

EXAMPLE 162

Ethyl 4-fluoro-2-nitrophenylthio-α,α'-dimethylacetate

Formula VIII: $R_1=4$-F; $R_3=R_4=CH_3$; $R_2=H$; $X=CH$; $Y=S$; $R''=C_2H_5$

Following the procedure of Example 19, but starting from 37.4 g of 4-fluoro-2-nitrophenylthio-α,α'-dimethylacetic acid prepared in Example 161, 38.5 g of ethyl 4-fluoro-2-nitrophenylthio-α,α'-dimethylacetate are obtained in the form of an oil which is used in the crude state for the next step.

EXAMPLE 163

6-Fluoro-2,2-dimethyl-2H-1,4-benzothiazin-3(4H)-one

Formula III: $R_1=6$-F; $R_3=R_4=CH_3$; $R_2=H$; $X=CH$; $Y=S$

Following the procedure of Example 28, but using 38.5 g of ethyl 4-fluoro-2-nitrophenylthio-α, α'-dimethylacetate prepared in Example 162, 18.5 g of 6-fluoro-2,2-dimethyl-2H-1,4-benzothiazin-3(4H)-one are obtained in the form of crystals of melting point 176° C.

EXAMPLE 164

Ethyl 6-fluoro-2,2-dimethyl-2H-1,4-benzothiazin-3-one-4-acetate

Formula II: $R_1=6$-F; $R_3=R_4=CH_3$; $R_2=H$; $X=CH$; $Y=S$; $Z=O$; $R'=C_2H_5$ Following the procedure of Example 52, but starting from 18.5 g of 6-fluoro-2,2-dimethyl-2H-1,4-benzothiazin-3(4H)-one prepared in Example 163, 25 g of ethyl 6-fluoro-2,2-dimethyl-2H-1,4-benzothiazin-3-one-4-acetate are obtained in the form of crystals of melting point 78° C.

EXAMPLE 165

Ethyl 6-fluoro-2,2-dimethyl-2H-1,4-benzothiazine-3-thione-4-acetate

Formula II: $R_1=6$-F; $R_3=R_4=CH_3$; $R_2=H$; $X=CH$; $Y=Z=S$; $R'=C_2H_5$

Following the procedure of Example 84, but starting from 18 g of ethyl 6-fluoro-2,2-dimethyl-2H-1,4-benzothiazin-3-one-4-acetate prepared in Example 168, 8 g of ethyl 6-fluoro-2,2-dimethyl-2H-1,4-benzothiazine-3-thione-4-acetate are obtained, after filtration on silica gel, elution with toluene and crystallization from pentane, in the form of crystals of melting point 60°–62° C.

EXAMPLE 166

6-Fluoro-2,2-dimethyl-2H-1,4-benzothiazin-3-one-4-acetic acid

Formula I: $R_1=6$-F; $R_3=R_4=CH_3$; $R_2=H$; $X=CH$; $Y=S$; $Z=O$

Following the procedure of Example 115, but starting from 7 g of ethyl 6-fluoro-2,2-dimethyl-2H-1,4-benzothiazin-3-one-4-acetate, Example 164, 4 g of 6-fluoro-2,2-dimethyl-2H-1,4-benzothiazin-3-one-4-acetic acid are obtained, after recrystallization from carbon tetrachloride, in the form of crystals of melting point 137°–138° C.

EXAMPLE 167

6-Fluoro-2,2-dimethyl-2H-1,4-benzothiazine-3-thione-4-acetic acid

Formula I: $R_1=6$-F; $R_3=R_4=CH_3$; $R_2=H$; $X=CH$; $Y=Z=S$

Following the procedure of Example 117, but starting from 7.8 g of ethyl 6-fluoro-2,2-dimethyl-2H-1,4-benzothiazine-3-thione-4-acetate prepared in Example 165, 5.8 g of 6-fluoro-2,2-dimethyl-2H-1,4-benzothiazine-3-thione-4-acetic acid are recovered in the form of crystals of melting point 171°–172° C.

EXAMPLE 168

(Preparation of a product according to the invention by hydrolysis using potassium bicarbonate)
2-Orthofluorophenyl-2H-1,4-benzothiazine-3-thione-4-acetic acid Code 5180-48

Formula I: $R_1=R_2=R_3=H$; $R_4=$orthofluorophenyl; $X=CH$; $Y=Z=S$

A solution of 5.6 g of ethyl 2-orthofluorophenyl-2H-1,4-benzothiazine-3-thione-4-acetate, obtained in Example 109, and 1.6 g of potassium bicarbonate in 100 ml of ethanol and 50 ml of water is heated under reflux for 3 hours. The solution is then cooled, treated with water and extracted with ether. The aqueous phase is then acidified in the cold with 0.1N hydrochloric acid and extracted with ether; this ether extract is dried over sodium sulfate and the ether is evaporated off in vacuo. The residue obtained crystallizes and the crystals are taken up with pentane and filtered off. 3.9 g of 2-orthofluorophenyl-2H-1,4-benzothiazine-3-thione-4-acetic acid are thus recovered in the form of crystals of melting point 180°–182° C., which are identical to those obtained in Example 160.

PHARMACOLOGY

Principle

The inhibitory activity on aldose reductase is evaluated in vitro starting from a rat lens homogenate used as a source of enzyme. The substrate used is DL-glyceraldehyde, which is converted by aldose reductase to glycerol in the presence of NADPH (*). This reaction is followed by spectrophotometry at 340 nm in the absence and in the presence of the inhibitors to be tested, the variation in optical density being proportional to the oxidation of the reduced coenzyme.

Results

The results are shown in Table I below and represent, for different examples, the percentage inhibition of the enzymatic activity, relative to the control activity, as a function of the different concentrations (mol.l$^{-1}$) used. The 50% inhibitory concentration was determined for the most active derivatives.

TABLE I

| Concentration (mol/liter) | $10^{-4}$ | $10^{-5}$ | $10^{-6}$ | $10^{-7}$ | $10^{-8}$ | $10^{-9}$ | IC$_{50}$ nm/l** |
|---|---|---|---|---|---|---|---|
| Inhibition relative to the control activity, % | | | | | | | |
| Example 110 | 95 | 82 | 37 | 11 | 4 | 9 | |
| Example 111 | 96 | 80 | | 5 | | | |
| Example 114 | 95 | 86 | 6 | | | | |
| Example 115 | 90 | 57 | | 3 | | | |
| Example 116 | 100 | 95 | 25 | | | | |

TABLE I-continued

| Concentration (mol/liter) | $10^{-4}$ | $10^{-5}$ | $10^{-6}$ | $10^{-7}$ | $10^{-8}$ | $10^{-9}$ | IC$_{50}$ nm/l** |
|---|---|---|---|---|---|---|---|
| Inhibition relative to the control activity, % | | | | | | | |
| Example 117 | 100 | 100 | | 65 | 5 | | 82 ± 1 |
| Example 118 | 98 | 91 | 10 | | | | |
| Example 119 | 100 | 98 | | 67 | 22 | | 46 ± 2 |
| Example 121 | 97 | 92 | 16 | | | | |
| Example 123 | 97 | 81 | 0 | | | | |
| Example 124 | 97 | 86 | 10 | | | | |
| Example 125 | 99 | 91 | 12 | | | | |
| Example 127 | | 98 | 93 | 28 | | | |
| Example 129 | | 74 | 25 | 5 | | | |
| Example 130 | | 99 | 95 | 17 | | | |
| Example 132 | | 95 | 92 | 16 | | | 42 ± 13*** |
| Example 133 | | 98 | 69 | 18 | | | 54 ± 5 |
| Example 136 | | 95 | 30 | 11 | | | |
| Example 137 | | 94 | 80 | 13 | | | |
| Example 151 | 96 | 73 | 16 | | | | |
| Example 152 | 100 | 99 | 54 | | | | 86 ± 4 |
| Example 154 | | 94 | 56 | 29 | | | 91 ± 15 |

*Nicotinamide Adenine Dinucleotide PHosphate, reduced form
**n = average of 3 determinations
***n = average of 2 determinations In human therapy, the compounds of the formula I and, if appropriate, their non-toxic addition salts can be administered, in particular orally, in the form of gelatin capsules or tablets containing from 50 to 300 mg of active principle.

These various compounds of the formula I or their non-toxic addition salts have an inhibitory activity on aldose reductase. They can therefore be beneficially administered for the treatment of certain complications of diabetes (cataract and peripheral neuropathies).

The products of the various examples described are of low toxicity in as much as the 50% lethal doses, determined by oral administration to rats, are all greater than 300 mg.kg$^{-1}$.

TABLE II

| Example 110 | CH$_2$COOH structure | Code 5155-01 |
| Example 111 | CH$_2$COOH structure | Code 5155-02 |
| Example 112 | CH$_2$COOH structure | Code 5155-06 |
| Example 113 | CH$_2$COOH structure | Code 5155-07 |

TABLE II-continued

| Example | Structure | Code |
|---|---|---|
| Example 114 | pyrido-pyrazinone with N-CH2COOH substituent ·HCl | Code 5155-03 |
| Example 115 | 5-CF3 benzothiazinone with N-CH2COOH | Code 5180-01 |
| Example 116 | 5-F benzothiazinone with N-CH2COOH | Code 5180-04 |
| Example 117 | 5-F benzothiazinethione with N-CH2COOH | Code 5180-09 |
| Example 118 | 6-F benzothiazinone with N-CH2COOH | Code 5180-10 |
| Example 119 | 6-F benzothiazinethione with N-CH2COOH | Code 5180-11 |
| Example 120 | 8-Cl benzothiazinone with N-CH2COOH | Code 5180-14 |
| Example 121 | 7-Cl benzothiazinone with N-CH2COOH | Code 5180-15 |
| Example 122 | 6-CH3O benzothiazinone with N-CH2COOH | Code 5180-16 |
| Example 123 | 5-CF3, 6-Cl benzothiazinone with N-CH2COOH | Code 5180-17 |
| Example 124 | benzothiazinone with N-CH2COOH | Code 5180-18 |
| Example 125 | 3-methyl benzothiazinone with N-CH2COOH | Code 5180-19 |
| Example 126 | 3-phenyl benzothiazinone with N-CH2COOH | Code 5180-20 |
| Example 127 | 7-Cl benzothiazinethione with N-CH2COOH | Code 5180-21 |
| Example 128 | 6-CH3O benzothiazinethione with N-CH2COOH | Code 5180-22 |
| Example 129 | 5-CF3, 6-Cl benzothiazinethione with N-CH2COOH | Code 5180-23 |
| Example 130 | 3-phenyl benzothiazinethione with N-CH2COOH | Code 5180-24 |
| Example 131 | 6-F3C benzothiazinethione with N-CH2COOH | Code 5180-25 |
| Example 132 | 3-methyl benzothiazinethione with N-CH2COOH | Code 5180-26 |
| Example 133 | benzothiazinethione with N-CH2COOH | Code 5180-27 |

TABLE II-continued

| Example | Structure | Code |
|---|---|---|
| Example 134 | 6-chloro-3-oxo-benzothiazine N-CH2COOH | Code 5180-28 |
| Example 135 | 6-chloro-3-thioxo-benzothiazine N-CH2COOH | Code 5180-29 |
| Example 136 | 6-fluoro-3-oxo-3-methyl-benzothiazine N-CH2COOH | Code 5180-30 |
| Example 137 | 6-fluoro-3-thioxo-3-methyl-benzothiazine N-CH2COOH | Code 5180-31 |
| Example 138 | 6-chloro-3-oxo-3-methyl-benzothiazine N-CH2COOH | Code 5180-32 |
| Example 139 | 6-chloro-3-oxo-3-phenyl-benzothiazine N-CH2COOH | Code 5180-33 |
| Example 140 | 6-chloro-3-thioxo-3-methyl-benzothiazine N-CH2COOH | Code 5180-34 |
| Example 141 | 3-oxo-3,3-dimethyl-benzothiazine N-CH2COOH | Code 5180-35 |
| Example 142 | 6-chloro-3-thioxo-3-phenyl-benzothiazine N-CH2COOH | Code 5180-36 |
| Example 143 | 3-oxo-3-(4-chlorophenyl)-benzothiazine N-CH2COOH | Code 5180-37 |
| Example 144 | 3-oxo-3-(2-chlorophenyl)-benzothiazine N-CH2COOH | Code 5180-38 |
| Example 145 | 6-chloro-3-oxo-3-methyl-benzothiazine N-CH2COOH | Code 5180-39 |
| Example 146 | 3-thioxo-3,3-dimethyl-benzothiazine N-CH2COOH | Code 5180-40 |
| Example 147 | 3-thioxo-3-(4-chlorophenyl)-benzothiazine N-CH2COOH | Code 5180-41 |
| Example 149 | 6,7-dichloro-3-thioxo-benzothiazine N-CH2COOH | Code 5180-42 |
| Example 150 | 6-chloro-3-thioxo-3-methyl-benzothiazine N-CH2COOH | Code 5180-43 |
| Example 148 | 3-thioxo-3-(2-chlorophenyl)-benzothiazine N-CH2COOH | Code 5180-44 |
| Example 157 | 3-oxo-3-(4-fluorophenyl)-benzothiazine N-CH2COOH | Code 5180-45 |

TABLE II-continued

| Example | Structure | Code |
|---|---|---|
| Example 158 | (2-fluorophenyl, phenyl-S, N-CH2COOH, C=O) | Code 5180-46 |
| Example 159 | (4-fluorophenyl, phenyl-S, N-CH2COOH, C=S) | Code 5180-47 |
| Example 160 | (2-fluorophenyl, phenyl-S, N-CH2COOH, C=S) | Code 5180-48 |
| Example 151 | (pyridyl, CH3, phenyl-S, N-CH2COOH, C=O) | Code 5177-01 |
| Example 152 | (F-phenyl-O, N-CH2COOH, C=S) | Code 5180-13 |
| Example 153 | (F-phenyl fused, N-CH2COOH, C=S) | Code 5204-04 |
| Example 154 | (Cl-phenyl fused, N-CH2COOH, C=S) | Code 5204-05 |
| Example 155 | (F-phenyl fused, N-CH2COOH, C=S) | Code 5204-07 |
| Example 156 | (Cl-phenyl fused, N-CH2COOH, C=S) | Code 5204-08 |

TABLE II-continued

| Example | Structure | Code |
|---|---|---|
| Example 166 | (5-fluorophenyl, S, N-CH2COOH, C=O, C(CH3)2) | Code 5180-49 |
| Example 167 | (5-fluorophenyl, S, N-CH2COOH, C=S, C(CH3)2) | Code 5180-50 |

What is claimed is:

1. A compound having the formula:

$$\text{structure with } R_1, R_2 \text{ on benzene ring, N-CH}_2\text{COOH, C=Z, R}_3, R_4, S$$

Z is sulfur;

$R_1$ and $R_2$ are selected from the group consisting of hydrogen, a halogen, trifluoromethyl, methoxy, thiomethyl, thiotrifluoromethyl and trifluoromethoxy; and $R_3$ and $R_4$ are selected from the group consisting of hydrogen, lower alkyl, phenyl, phenyl substituted with a halogen, pyridyl and pyridyl substituted with a halogen; and the nontoxic addition salts thereof.

2. The compound of claim 1 wherein $R_1$ is hydrogen and $R_2$ is fluorine.

3. The compound of claim 1 wherein $R_3$ is hydrogen and $R_4$ is methyl.

4. The compound of claim 1 wherein $R_3$ is hydrogen and $R_4$ is phenyl.

5. The compound of claim 1 wherein $R_1$, $R_3$ and $R_4$ are hydrogen.

6. The compound of claim 5 wherein $R_2$ is fluorine.

7. The compound of claim 5 wherein $R_2$ is chlorine.

8. The compound of claim 5 wherein $R_2$ is hydrogen.

9. The compound of claim 1 wherein $R_1$ is fluorine and $R_2$, $R_3$ and $R_4$ are hydrogen.

10. The compound of claim 1 wherein $R_1$, $R_2$ and $R_3$ are hydrogen.

11. The compound of claim 10 wherein $R_4$ is phenyl.

12. The compound of claim 10 wherein $R_4$ is methyl.

13. The compound of claim 1 wherein $R_1$ and $R_3$ are hydrogen, $R_2$ is fluorine and $R_4$ is phenyl.

14. The compound of claim 1 wherein $R_1$ and $R_3$ are hydrogen, $R_2$ is fluorine and $R_4$ is methyl.

15. The compound of claim 1 wherein $R_1$ is fluorine, $R_2$ and $R_3$ are hydrogen, and $R_4$ is methyl.

16. A pharmaceutical composition comprising:
an excipient; and
an effective amount of a compound selected from the group consisting of compounds having the formula:

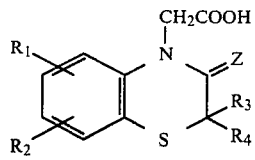

wherein,

Z is sulfur;

$R_1$ and $R_2$ are selected from the group consisting of hydrogen, a halogen, trifluoromethyl, methoxy, thiomethyl, thiotrifluoromethyl and trifluoromethoxy; and $R_3$ and $R_4$ are selected from the group consisting of hydrogen, lower alkyl, phenyl, phenyl substituted with a halogen, pyridyl and pyridyl substituted with a halogen; and the nontoxic addition salts thereof.

17. A process for inhibiting aldose reductase comprising reacting the aldose reductase with an effective amount of a compound selected from the group consisting of compounds having the formula:

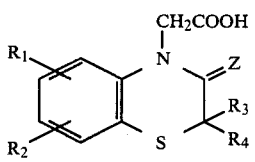

wherein,

Z is sulfur;

$R_1$ and $R_2$ are selected from the group consisting of hydrogen, a halogen, trifluoromethyl, methoxy, thiomethyl, thiotrifluoromethyl and trifluoromethoxy; and $R_3$ and $R_4$ are selected from the group consisting of hydrogen, lower alkyl, phenyl, phenyl substituted with a halogen, pyridyl and pyridyl substituted with a halogen; and the nontoxic addition salts thereof.

18. The compound of claim 1 wherein $R_1$ is hydrogen and $R_2$ if flourine.

19. The compound of claim 1 wherein $R_3$ is hydrogen and $R_4$ is methyl.

20. The compound of claim 1 wherein $R_3$ is hydrogen and $R_4$ is phenyl.

21. A compound having the formula:

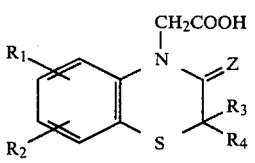

wherein,

Z is selected from the group consisting of sulfur and oxygen;

$R_1$ and $R_2$ are selected from the group consisting of hydrogen, a halogen, trifluoromethyl, methoxy, thiomethyl, thiotrifluoromethyl and trifluoromethoxy; and $R_3$ and $R_4$ are selected from the group consisting of hydrogen, lower alkyl, pyridyl and pyridyl substituted with a halogen; and the nontoxic addition salts thereof.

22. A compound having the formula:

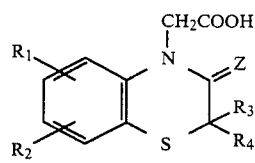

wherein,

Z is selected from the group consisting of sulfur and oxygen;

$R_1$ and $R_2$ are selected from the group consisting of hydrogen, a halogen, trifluoromethyl, methoxy, thiomethyl, thiotrifluoromethyl and trifluoromethoxy; and $R_3$ and $R_4$ are selected from the group consisting of hydrogen and lower alkyl; and the nontoxic addition salts thereof.

23. A compound having the formula:

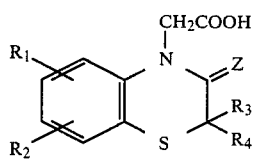

wherein,

Z is oxygen;

$R_1$ and $R_2$ are selected from the group consisting of hydrogen, a halogen, trifluoromethyl, methoxy, thiomethyl, thiotrifluoromethyl and trifluoromethoxy; and $R_3$ and $R_4$ are selected from the group consisting of hydrogen, lower alkyl, phenyl, phenyl substituted with a halogen, pyridyl and pyridyl substituted with a halogen; and the nontoxic addition salts thereof.

24. A pharmaceutical composition comprising:

an excipient; and an effective amount of a compound selected from the group consisting of compounds having the formula:

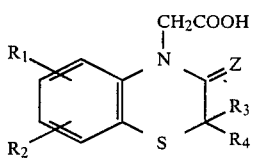

wherein,

Z is selected from the group consisting of sulfur and oxygen;

$R_1$ and $R_2$ are selected from the group consisting of hydrogen, a halogen, trifluoromethyl, methoxy, thiomethyl, thiotrifluoromethyl and trifluoromethoxy; and $R_3$ and $R_4$ are selected from the group consisting of hydrogen, lower alkyl, pyridyl and pyridyl substituted with a halogen; and the nontoxic addition salts thereof.

25. A pharmaceutical composition comprising:

an excipient; and an effective amount of a compound selected from the group consisting of compounds having the formula:

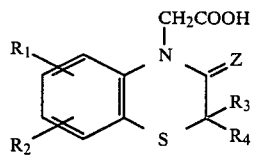

wherein,

Z is selected from the group consisting of sulfur and oxygen;

$R_1$ and $R_2$ are selected from the group consisting of hydrogen, a halogen, trifluoromethyl, methoxy, thiomethyl, thiotrifluoromethyl and trifluoromethoxy; and $R_3$ and $R_4$ are selected from the group consisting of hydrogen and lower alkyl; and the nontoxic addition salts thereof.

26. A pharmaceutical composition comprising:

an excipient; and an effective amount of a compound selected from the group consisting of compounds having the formula:

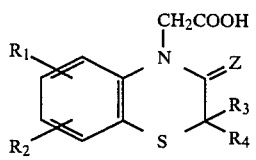

wherein,

Z is oxygen;

$R_1$ and $R_2$ are selected from the group consisting of hydrogen, a halogen, trifluoromethyl, methoxy, thiomethyl, thiotrifluoromethyl and trifluoromethoxy; and $R_3$ and $R_4$ are selected from the group consisting of hydrogen, lower alkyl, phenyl, phenyl substituted with a halogen, pyridyl and pyridyl substituted with a halogen; and the nontoxic addition salts thereof.

27. A process for inhibiting aldose reductase comprising reacting the aldose reductase with an effective amount of a compound selected from the group consisting of compounds of the formula:

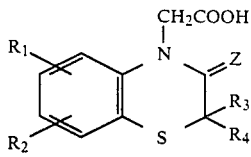

wherein,

Z is selected from the group consisting of sulfur and oxygen;

$R_1$ and $R_2$ are selected from the group consisting of hydrogen, a halogen, trifluoromethyl, methoxy, thiomethyl, thiotrifluoromethyl and trifluoromethoxy; and $R_3$ and $R_4$ are selected from the group consisting of hydrogen, lower alkyl, pyridyl and pyridyl substituted with a halogen; and the nontoxic addition salts thereof.

28. A process for inhibiting aldose reductase comprising reacting the aldose reductase with an effective amount of a compound selected from the group consisting of compounds of the formula:

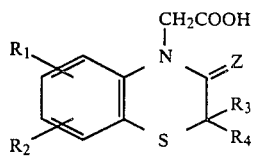

wherein,

Z is selected from the group consisting of sulfur and oxygen;

$R_1$ and $R_2$ are selected from the group consisting of hydrogen, a halogen, trifluoromethyl, methoxy, thiomethyl, thiotrifluoromethyl and trifluoromethoxy; and $R_3$ and $R_4$ are selected from the group consisting of hydrogen and lower alkyl; and the nontoxic addition salts thereof.

29. A process for inhibiting aldose reductase comprising reacting the aldose reductase with a effective amount of a compound selected from the group consisting of compounds having the formula:

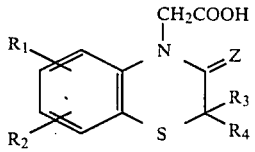

wherein,

Z is oxygen;

$R_1$ and $R_2$ are selected from the group consisting of hydrogen, a halogen, trifluoromethyl, methoxy, thiomethyl, thiotrifluoromethyl and trifluoromethoxy; and $R_3$ and $R_4$ are selected from the group consisting of hydrogen, lower alkyl, phenyl, phenyl substituted with a halogen, pyridyl and pyridyl substituted with a halogen; and the nontoxic addition salts thereof.

* * * * *

UNITED STATES PATENT AND TRADEMARK OFFICE
CERTIFICATE OF CORRECTION

PATENT NO. : 4,755,509

DATED : July 5, 1988

INVENTOR(S) : Jean-Marie Teulon

It is certified that error appears in the above-identified patent and that said Letters Patent is hereby corrected as shown below:

IN EXAMPLE 13

In column 6, line 29, please delete "VII" and substitute therefor --VIII--.

IN EXAMPLE 18

In column 7, line 32, please delete "$CH_2$" and substitute therefor --$C_2$--.

IN EXAMPLE 22

In column 8, line 31, please delete "$R_4H$" and substitute therefor --$R_4=H$--.

In column 8, line 40, please delete "following" and substitute therefor --followed--.

UNITED STATES PATENT AND TRADEMARK OFFICE
CERTIFICATE OF CORRECTION

PATENT NO. : 4,755,509

DATED : July 5, 1988

INVENTOR(S) : Jean-Marie Teulon

It is certified that error appears in the above-identified patent and that said Letters Patent is hereby corrected as shown below:

IN EXAMPLE 38

In column 11, line 38, please delete "3(4)" and substitute therefor --3(4H)--.

IN EXAMPLE 45

In column 12, line 68, please delete "either" and substitute therefor --ether--.

IN EXAMPLE 99

In column 23, line 52, please delete "procedurre" and substitute therefor --procedure--.

IN EXAMPLE 132

In column 30, line 23, please delete "$R_3H$" and substitute therefor --$R_3=H$--.

IN EXAMPLE 161

In column 35, line 67, please delete "nitrophenyl" and substitute therefor --nitrophenylthio--.

UNITED STATES PATENT AND TRADEMARK OFFICE
CERTIFICATE OF CORRECTION

PATENT NO. : 4,755,509

DATED : July 5, 1988

INVENTOR(S) : Jean-Marie Teulon

It is certified that error appears in the above-identified patent and that said Letters Patent is hereby corrected as shown below:

<u>IN EXAMPLE 165</u>

In column 36, line 52, please delete "168" and substitute therefor --164--.

<u>IN THE CLAIMS</u>

In column 44, line 25, please insert --wherein,--.

Signed and Sealed this

Twenty-ninth Day of January, 1991

*Attest:*

HARRY F. MANBECK, JR.

*Attesting Officer*      *Commissioner of Patents and Trademarks*